United States Patent
Cundiff et al.

(10) Patent No.: US 12,064,127 B2
(45) Date of Patent: Aug. 20, 2024

(54) SURGICAL CUTTING BLOCK INCLUDING MULTIPLE CUT GUIDES

(71) Applicant: Fusion Orthopedics USA, LLC, Mesa, AZ (US)

(72) Inventors: Adam J. Cundiff, Gilbert, AZ (US); Nathan G. Peterson, Gilbert, AZ (US); Kolby K. Black, Spanish Fork, UT (US); Mark William Roberts, Jr., Gilbert, AZ (US); Eli W. Jacobson, Chandler, AZ (US)

( * ) Notice: Subject to any disclaimer, the term of this patent is extended or adjusted under 35 U.S.C. 154(b) by 185 days.

(21) Appl. No.: 17/182,125

(22) Filed: Feb. 22, 2021

(65) Prior Publication Data

US 2022/0151642 A1   May 19, 2022

Related U.S. Application Data

(60) Provisional application No. 63/115,187, filed on Nov. 18, 2020.

(51) Int. Cl.
| | | |
|---|---|---|
| *A61B 17/17* | (2006.01) | |
| *A61B 17/15* | (2006.01) | |
| *A61B 17/56* | (2006.01) | |
| *A61B 17/84* | (2006.01) | |

(52) U.S. Cl.
CPC ............ *A61B 17/17* (2013.01); *A61B 17/151* (2013.01); *A61B 17/152* (2013.01); *A61B 17/1775* (2016.11); *A61B 17/56* (2013.01); *A61B 2017/564* (2013.01); *A61B 2017/565* (2013.01); *A61B 2017/567* (2013.01); *A61B 2017/568* (2013.01); *A61B 17/842* (2013.01)

(58) Field of Classification Search
CPC ... A61B 17/17; A61B 17/1775; A61B 17/151; A61B 17/152; A61B 17/15; A61B 17/56; A61B 2017/565; A61B 2017/564; A61B 2017/567; A61B 2017/568; A61B 17/842
USPC .......................................................... 606/87
See application file for complete search history.

(56) References Cited

U.S. PATENT DOCUMENTS

| | | | |
|---|---|---|---|
| D695,402 S | * | 12/2013 | Dacosta ....................... D24/155 |
| 9,622,805 B2 | | 4/2017 | Santrock et al. |
| 9,687,250 B2 | | 6/2017 | Dayton et al. |
| 9,936,994 B2 | | 4/2018 | Smith et al. |
| 10,045,807 B2 | | 8/2018 | Santrock et al. |
| 10,159,499 B2 | | 12/2018 | Dacosta et al. |
| 10,335,220 B2 | | 7/2019 | Smith |

(Continued)

*Primary Examiner* — Marcela I. Shirsat

(57) ABSTRACT

Various surgical cutting blocks are presented herein. One surgical cutting block includes a cutting platform including a positioning aperture formed on the cutting platform in which the positioning platform divides the cutting platform into first and second sides and the first side and/or the second side includes multiple single cut guides formed thereon. Another surgical cutting block includes a cutting platform including a positioning aperture formed on the cutting platform in which the positioning platform divides the cutting platform into first and second sides and the first side and/or the second side incudes a double cut guide formed thereon. Yet another surgical cutting block includes a cutting platform including a positioning aperture formed on the cutting platform in which the positioning platform divides the cutting platform into first and second sides and the first side and/or the second side includes a multi-cut guide formed thereon.

15 Claims, 23 Drawing Sheets

(56) References Cited

U.S. PATENT DOCUMENTS

| | | |
|---|---|---|
| 10,342,590 B2 | 7/2019 | Bays et al. |
| 10,512,470 B1 | 12/2019 | Bays et al. |
| 10,524,808 B1 | 1/2020 | Hissong et al. |
| 10,555,757 B2 | 2/2020 | Dayton |
| 10,561,426 B1 | 2/2020 | Dayton et al. |
| 10,575,862 B2 | 3/2020 | Bays et al. |
| 10,582,936 B1 | 3/2020 | Hissong et al. |
| 10,603,046 B2 | 3/2020 | Dayton et al. |
| 10,849,631 B2 | 12/2020 | Hatch et al. |
| 10,849,663 B2 | 12/2020 | Dayton et al. |
| 10,849,670 B2 | 12/2020 | Santrock et al. |
| 10,874,446 B2 | 12/2020 | Smith et al. |
| 10,888,335 B2 | 1/2021 | Dayton et al. |
| 10,939,939 B1 | 3/2021 | Gil et al. |
| 10,945,764 B2 | 3/2021 | Dayton et al. |
| 11,039,873 B2 | 6/2021 | Santrock et al. |
| 11,076,863 B1 | 8/2021 | Bays et al. |
| 11,116,558 B2 | 9/2021 | Smith et al. |
| 11,147,590 B2 | 10/2021 | Dayton et al. |
| 2016/0015426 A1 | 1/2016 | Dayton |
| 2016/0242791 A1* | 8/2016 | Fallin ............... A61B 17/151 |
| 2017/0079669 A1* | 3/2017 | Bays ............... A61B 17/1739 |
| 2018/0132868 A1 | 5/2018 | Dacosta et al. |
| 2018/0289423 A1* | 10/2018 | Singh ............... A61B 34/10 |
| 2019/0328435 A1 | 10/2019 | Bays et al. |
| 2019/0336140 A1* | 11/2019 | Dacosta ............... A61B 17/15 |
| 2020/0015856 A1 | 1/2020 | Treace et al. |
| 2020/0029977 A1 | 1/2020 | Dayton et al. |
| 2020/0155176 A1 | 5/2020 | Bays et al. |
| 2020/0205844 A1 | 7/2020 | Hissong et al. |
| 2020/0253641 A1 | 8/2020 | Treace et al. |
| 2021/0038212 A1 | 2/2021 | May et al. |
| 2021/0093328 A1 | 4/2021 | Dayton et al. |
| 2021/0093365 A1 | 4/2021 | Dayton et al. |
| 2021/0236180 A1 | 8/2021 | DeCarbo et al. |
| 2021/0251659 A1 | 8/2021 | Gil et al. |

\* cited by examiner

SURGICAL CUTTING BLOCK INCLUDING MULTIPLE CUT GUIDES

REFERENCE TO RELATED APPLICATION

This application claims priority to and the benefit of U.S. Provisional Patent Application No. 63/115,187, filed on Nov. 18, 2020, the contents of which are incorporated herein by reference in their entirety.

FIELD OF THE TECHNOLOGY

The present technology relates generally to surgical instruments, and more particularly to, a surgical cutting block including a plurality of cut guides.

BACKGROUND

Different surgical procedures utilize different instruments and techniques. In an osteotomy for correcting a bunion, for example, the surgeon makes multiple cuts to the bone to realign the joint using multiple surgical cutting blocks that each include a single cutting guide. That is, each time that a new cut is needed to be made to the bone, the surgeon must move the surgical cutting block to a new location or use a different surgical cutting block at the new location to make the cut, both of which are time consuming and/or an inefficient use of surgical instrumentation.

SUMMARY

Various embodiments provide a surgical cutting block including a plurality of cut guides. One surgical cutting block includes a cutting platform including a positioning aperture formed on the cutting platform in which the positioning platform divides the cutting platform into a first side and a second side. The surgical cutting block further includes plurality of single cut guides formed on the first side and/or the second side.

Another surgical cutting block includes a cutting platform including a positioning aperture formed on the cutting platform in which the positioning platform divides the cutting platform into a first side and a second side. The surgical cutting block further incudes a double cut guide formed on the first side and/or the second side.

Yet another surgical cutting block includes a cutting platform including a positioning aperture formed on the cutting platform in which the positioning platform divides the cutting platform into a first side and a second side. The surgical cutting block further includes a multi-cut guide formed on the first side and/or the second side.

BRIEF DESCRIPTION OF THE DRAWINGS

To readily understand the advantages and benefits of the technology, a more particular description of the technology briefly described above will be rendered by reference to specific embodiments that are illustrated in the appended drawings. Understanding that these drawings depict typical embodiments of the technology, and are therefore not to be considered to be limiting of its scope, the technology will be described and explained with additional specificity and detail through the use of the accompanying drawings, in which.

DETAILED DESCRIPTION OF THE DRAWINGS

It should be understood that the language used in the present disclosure has been principally selected for read-ability and instructional purposes, and not to limit the scope of the subject matter disclosed herein in any manner. Further, reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including, but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

In addition, as used herein, the term "set" can mean "one or more," unless expressly specified otherwise. The term "sets" can mean multiples of or a plurality of "one or mores," "ones or more," and/or "ones or mores" consistent with set theory, unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

The present technology includes surgical cutting blocks and positioning fins. Furthermore, the described features, structures, or characteristics of the various embodiments disclosed herein may be combined in any suitable manner. One skilled in the relevant art will recognize, however, that embodiments may be practiced without one or more of the specific details, or with other methods, components, materials, and so forth. In other instances, well-known structures, and/or materials are not shown or described in detail to avoid obscuring aspects of an embodiment.

Figure 1:
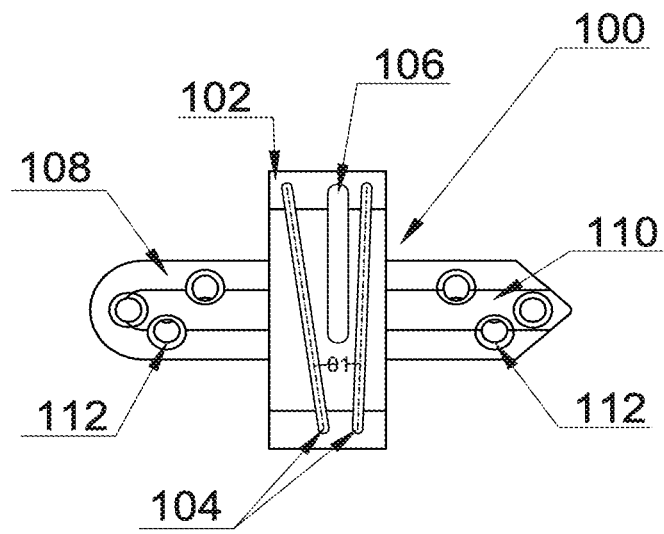
FIG. 1 is a diagram illustrating one embodiment of a surgical cutting block including a plurality of single cut guides.

Turning now to the drawings, FIG. 1 is a diagram illustrating one embodiment of a surgical cutting block 100. At least in the illustrated embodiment, the surgical cutting block 100 includes, among other components, a cutting platform 102 (or cutting portion 102) including a plurality of single cut guides 104 (e.g., cutting slots) formed thereon, a positioning slot 106 (e.g., an aperture), a cuneiform fixation platform 108, a metatarsal fixation platform 110, and a plurality of wire holes 112.

The cutting platform 102 may be formed of any suitable material. In certain embodiments, the material included in and/or forming the cutting platform 102 is sterilizable.

In the embodiment illustrated in FIG. 1, the plurality of single cut guides 104 includes a single cut guide 104 located on opposite sides of the positioning slot 106. Other embodiments may include the plurality of single cut guides 104 positioned at other locations on the cutting platform 102 (e.g., on the same side of the positioning slot 106, among other locations that are possible and contemplated herein). That is, the plurality of single cut guides 104 may be positioned/formed at any suitable location on the cutting platform 102.

The single cut guides 104 each include a size and/or width capable of accepting a surgical cutting tool (e.g., a scalpel, surgical knife, etc.) and provide a single path for the surgical cutting tool to follow while the surgical cutting tool is being used to produce an incision in a patient. Each single cut guide 104 includes an angle (θ), which can be any suitable angle (e.g., an angle (θ) in the range of about one degree (1°) to about 90 degrees (90°)) with respect to any suitable reference point that can provide a predetermined and/or target path for the surgical cutting tool to follow while the surgical cutting tool is cutting a patient and/or performing a surgical procedure.

In some embodiments, all of the single cut guides 104 are angled in the same direction (e.g., angled toward the left or toward the right with respect to the user (e.g., a medical professional)). In the illustrated embodiment, all of the single cut guides 104 are angled in the different directions (see, e.g., FIG. 1).

In additional or alternative embodiments, a pair of single cut guides 104 are positioned on the cutting platform 102 such that there is an angle ($\theta_1$) created between the pair of single cut guides 104, which may be any suitable angle ($\theta_1$). In various embodiments, the angle ($\theta_1$) is in the range of about fifteen degrees (15°) to about 75 degrees (75°).

The positioning slot 106 is configured to facilitate positioning the surgical cutting block 100 over a target surgical area. The positioning slot 106 may include any suitable size and/or shape that can facilitate positioning the surgical cutting block 100 over a target surgical area.

A cuneiform fixation platform 108 may include any suitable size, shape, and/or material(s) that can facilitate fixating the surgical cutting block 100 to a cuneiform. In certain embodiments, the cuneiform fixation platform 108 is located on a side of the cutting platform 102, among other locations that are possible and contemplated herein.

A metatarsal fixation platform 110 may include any suitable size, shape, and/or material(s) that can facilitate fixating the surgical cutting block 100 to a metatarsal. In various embodiments, the metatarsal fixation platform 110 is located on a side of the cutting platform 102, among other locations that are possible and contemplated herein. In some embodiments, the cuneiform fixation platform 108 is located on one side of the cutting platform 102 and the metatarsal fixation platform 110 is located on the other side of the cutting platform 102 opposite the cuneiform fixation platform 108, among other locations and/or relative positions that are possible and contemplated herein.

In some embodiments, the cuneiform fixation platform 108 and the metatarsal fixation platform 110 include a set of wire holes 112 formed respectively therein. Each of the the cuneiform fixation platform 108 and the metatarsal fixation platform 110 include one or more wire holes 112 for attaching the surgical cutting block 100 to a cuneiform and a metatarsal, respectively, which can be any suitable quantity of wire holes 112. Further, the wire holes 112 may include any suitable size and/or shape that can facilitate fixating the surgical cutting block 100 to a cuneiform and a metatarsal via a pin passing through the wire holes 112 on the cuneiform fixation platform 108 and the metatarsal fixation platform 110, respectively.

Figure 2:
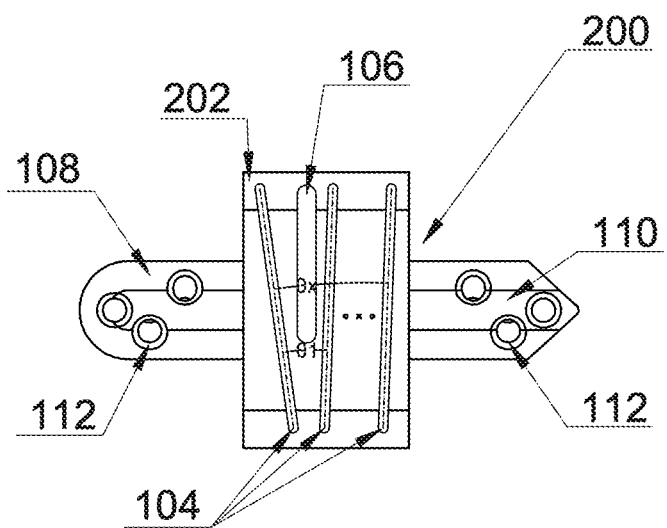
FIG. 2 is a diagram illustrating another embodiment of a surgical cutting block including a plurality of single cut guides.

FIG. 2 is a diagram illustrating another embodiment of a surgical cutting block 200 including a plurality of single cut guides 104. In this embodiment, a sub-plurality of single cut guides 104 are positioned/located on a cutting platform 202 on the side of the positioning slot 106 toward the metatarsal fixation platform 110. Further, surgical cutting block 200 includes one single cut guide 104 positioned/located on the cutting platform 202 on the side of the positioning slot 106 toward the cuneiform fixation platform 108.

In some embodiments, all of the single cut guides 104 are angled in the same direction (e.g., angled toward the left or toward the right with respect to the user (e.g., a medical professional)). In the illustrated embodiment, all of the single cut guides 104 on the same side of the positioning slot 106 are angled in the same direction and in a different direction than the single cut guide 104 on the other side of the positioning slot 106.

In additional or alternative embodiments, the single cut guides 104 are positioned on the cutting platform 202 such that there is an angle ($\theta_1$) and ($\theta_x$) created between the sub-plurality of single cut guides 104 and the one single cut guide 104, which may be any suitable angle. In various embodiments, the respective angles ($\theta_1$) and ($\theta_x$) may each be in the range of about fifteen degrees (15°) to about 75 degrees (75°).

Figure 3:
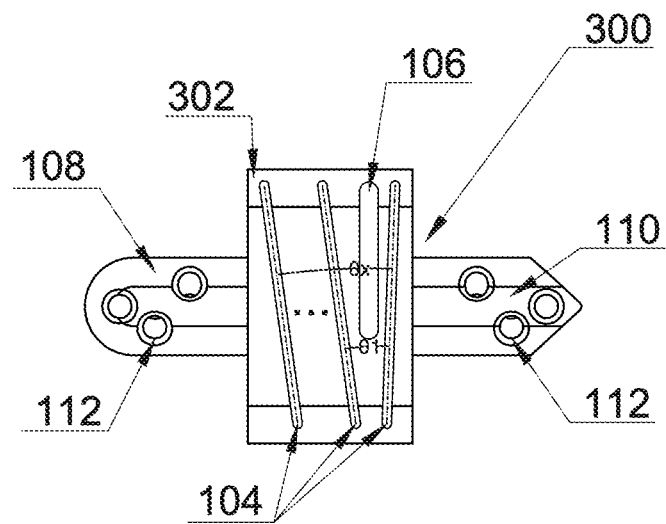
FIG. 3 is a diagram illustrating yet another embodiment of a surgical cutting block including a plurality of single cut guides.

FIG. 3 is a diagram illustrating yet another embodiment of a surgical cutting block 300 including a plurality of single cut guides 104. In this embodiment, a sub-plurality of single cut guides 104 are positioned/located on a cutting platform 302 on the side of the positioning slot 106 toward the cuneiform fixation platform 108. Further, surgical cutting block 300 includes one single cut guide 104 positioned/located on the cutting platform 302 on the side of the positioning slot 106 toward the metatarsal fixation platform 110.

In some embodiments, all of the single cut guides 104 are angled in the same direction (e.g., angled toward the left or toward the right with respect to the user (e.g., a medical professional)). In the illustrated embodiment, all of the single cut guides 104 on the same side of the positioning slot 106 are angled in the same direction and in a different direction than the single cut guide 104 on the other side of the positioning slot 106.

In additional or alternative embodiments, the single cut guides 104 are positioned on the cutting platform 302 such that there is an angle ($\theta_1$) and ($\theta_x$) created between the sub-plurality of single cut guides 104 and the one single cut guide 104, which may be any suitable angle. In various embodiments, the respective angles ($\theta_1$) and ($\theta_x$) may each be in the range of about 15° to about 75°.

Figure 4:
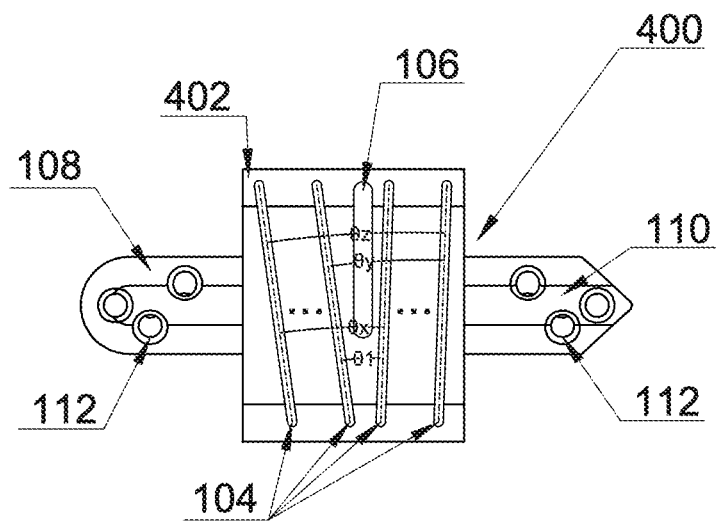
FIG. 4 is a diagram illustrating still another embodiment of a surgical cutting block including a plurality of single cut guides.

FIG. 4 is a diagram illustrating still another embodiment of a surgical cutting block 400 including a plurality of single cut guides 104. In this embodiment, a sub-plurality of single cut guides 104 are positioned/located on a cutting platform 402 on the side of the positioning slot 106 toward the metatarsal fixation platform 110. Further, surgical cutting block 400 includes a sub-plurality of single cut guides 104 positioned/located on the cutting platform 102 on the side of the positioning slot 106 toward the cuneiform fixation platform 108.

In some embodiments, all of the single cut guides 104 are angled in the same direction (e.g., angled toward the left or toward the right with respect to the user (e.g., a medical professional)). In the illustrated embodiment, all of the single cut guides 104 on the same side of the positioning slot 106 are angled in the same direction and in a different direction than the single cut guides 104 on the other side of the positioning slot 106.

In additional or alternative embodiments, the single cut guides 104 are positioned on the cutting platform 402 such that there is an angle ($\theta_1$), ($\theta_x$), ($\theta_y$), and (Oz) created between the sub-plurality of single cut guides 104 located on each side of the positioning slot 106, which may be any suitable angle. In various embodiments, the respective angles ($\theta_1$), ($\theta_x$), ($\theta_y$), and (Oz) may each be in the range of about 15° to about 75°.

Figure 5:
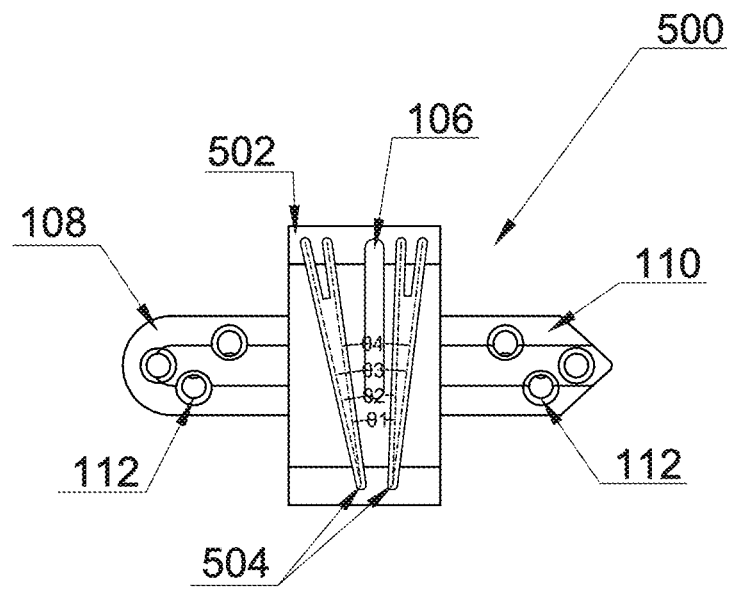
FIG. 5 is a diagram illustrating one embodiment of a surgical cutting block including a plurality of double cut guides.

FIG. 5 is a diagram illustrating one embodiment of a surgical cutting block 500 including a plurality of double cut guides 104. In this embodiment, a double cut guide 504 is positioned/located on a cutting platform 502 on each side of the positioning slot 106, among other positions that are possible and contemplated herein.

The double cut guides 504 each include a pair of paths that can include any suitable size and/or width capable of accepting a surgical cutting tool (e.g., a scalpel, surgical knife, etc.) and provide a respective path for the surgical cutting tool to follow while the surgical cutting tool is being used to produce an incision in a patient. Each double cut guide 504 includes an angle, which can be any suitable angle (e.g., an angle in the range of about one degree (1°) to about 90 degrees (90°)) with respect to any suitable reference point that can provide a predetermined and/or target path for the surgical cutting tool to follow while the surgical cutting tool is cutting a patient and/or performing a surgical procedure.

In some embodiments, all of the double cut guides 504 are angled in the same direction (e.g., angled toward the left or toward the right with respect to the user (e.g., a medical professional)). In the illustrated embodiment, all of the double cut guides 504 are angled in the different directions.

In additional or alternative embodiments, a pair of double cut guides 504 are positioned on the cutting platform 502 such that there is an angle ($\theta_1$), ($\theta_2$), ($\theta_3$), and ($\theta_4$) created between the double cut guides 504 located on each side of the positioning slot 106, which may be any suitable angle. In various embodiments, the respective angles ($\theta_1$), ($\theta_2$), ($\theta_3$), and ($\theta_4$) may each be in the range of about 15° to about 75°.

Figure 6:
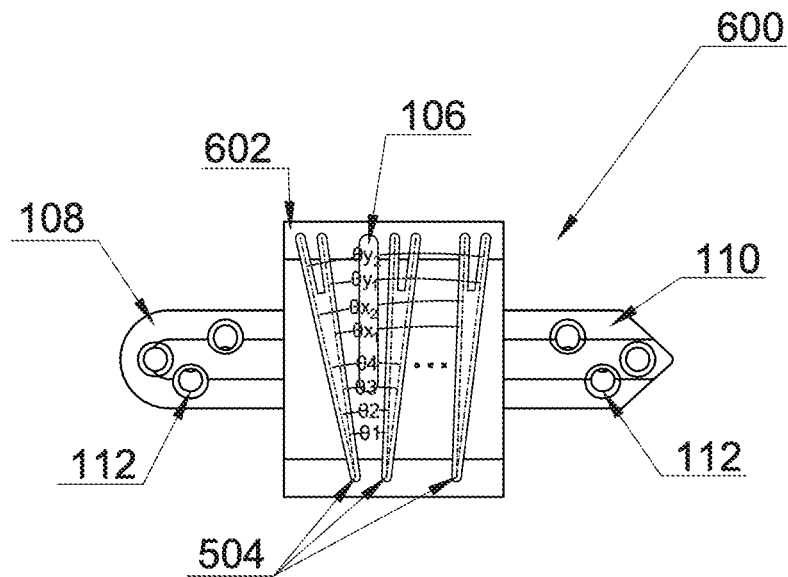
FIG. 6 is a diagram illustrating another embodiment of a surgical cutting block including a plurality of double cut guides.

FIG. 6 is a diagram illustrating another embodiment of a surgical cutting block 600 including a plurality of double cut guides 504. In this embodiment, a sub-plurality of double cut guides 504 are positioned/located on a cutting platform 602 on the side of the positioning slot 106 toward the metatarsal fixation platform 110. Further, surgical cutting block 600 includes one double cut guide 504 positioned/located on the cutting platform 602 on the side of the positioning slot 106 toward the cuneiform fixation platform 108.

In some embodiments, all of the double cut guides 504 are angled in the same direction (e.g., angled toward the left or toward the right with respect to the user (e.g., a medical professional)). In the illustrated embodiment, all of the double cut guides 504 on the same side of the positioning slot 106 are angled in the same direction and in a different direction than the double cut guide 504 on the other side of the positioning slot 106.

In additional or alternative embodiments, the double cut guides 504 are positioned on the cutting platform 602 such that there is an ($\theta_1$), ($\theta_2$), ($\theta_3$), ($\theta_4$), ($\theta_{x1}$), ($\theta_{x2}$), ($\theta_{y1}$), and ($\theta_{y2}$) created between the double cut guides 504 located on each side of the positioning slot 106, which may be any suitable angle. In various embodiments, the respective angles ($\theta_1$), ($\theta_2$), ($\theta_3$), ($\theta_4$), ($\theta_{x1}$), ($\theta_{x2}$), ($\theta_{y1}$), and ($\theta_{y2}$) may each be in the range of about 15° to about 75°.

Figure 7:
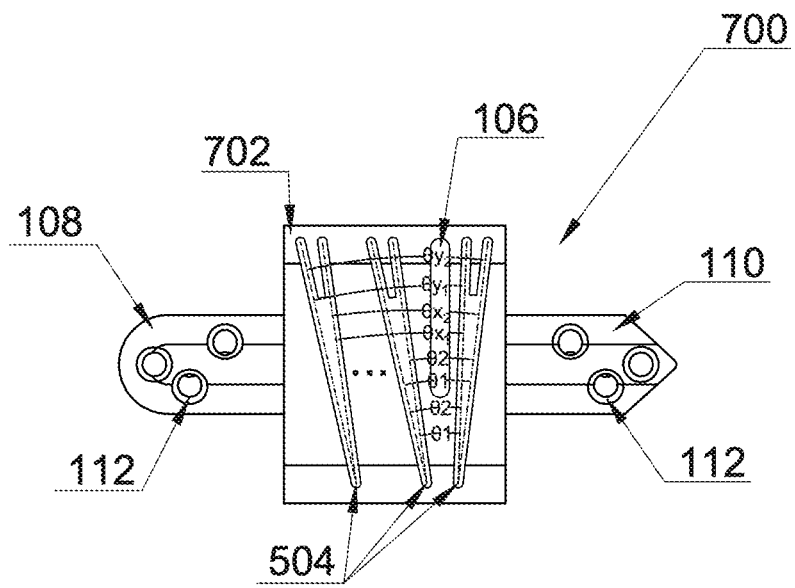
FIG. 7 is a diagram illustrating yet another embodiment of a surgical cutting block including a plurality of double cut guides.

FIG. 7 is a diagram illustrating another embodiment of a surgical cutting block 700 including a plurality of double cut guides 504. In this embodiment, a sub-plurality of double cut guides 504 are positioned/located on a cutting platform 702 on the side of the positioning slot 106 toward the cuneiform fixation platform 108. Further, surgical cutting block 700 includes one double cut guide 504 positioned/located on the cutting platform 702 on the side of the positioning slot 106 toward the metatarsal fixation platform 110.

In some embodiments, all of the double cut guides 504 are angled in the same direction (e.g., angled toward the left or toward the right with respect to the user (e.g., a medical professional)). In the illustrated embodiment, all of the double cut guides 504 on the same side of the positioning slot 106 are angled in the same direction and in a different direction than the double cut guide 504 on the other side of the positioning slot 106.

In additional or alternative embodiments, the double cut guides 504 are positioned on the cutting platform 702 such that there is an ($\theta_1$), ($\theta_2$), ($\theta_3$), ($\theta_4$), ($\theta_{x1}$), ($\theta_{x2}$), ($\theta_{y1}$), and ($\theta_{y2}$) created between the double cut guides 504 located on each side of the positioning slot 106, which may be any suitable angle. In various embodiments, the respective angles ($\theta_1$), ($\theta_2$), ($\theta_3$), ($\theta_4$), ($\theta_{x1}$), ($\theta_{x2}$), ($\theta_{y1}$), and ($\theta_{y2}$) may each be in the range of about 15° to about 75°.

Figure 8:
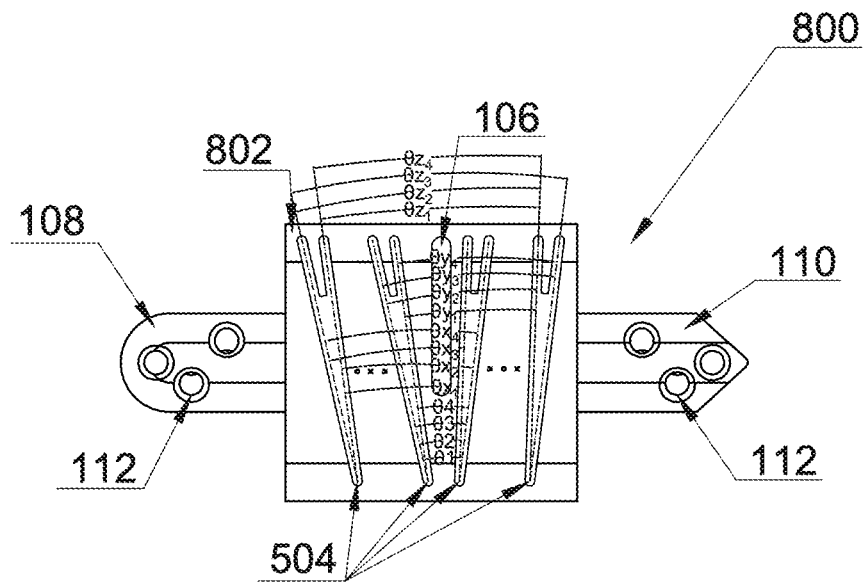
FIG. 8 is a diagram illustrating still another embodiment of a surgical cutting block including a plurality of double cut guides.

FIG. 8 is a diagram illustrating another embodiment of a surgical cutting block 800 including a plurality of double cut guides 504. In this embodiment, a sub-plurality of double cut guides 504 are positioned/located on a cutting platform 802 on both sides of the positioning slot.

In some embodiments, all of the double cut guides 504 are angled in the same direction (e.g., angled toward the left or toward the right with respect to the user (e.g., a medical professional)). In the illustrated embodiment, all of the double cut guides 504 on the same side of the positioning slot 106 are angled in the same direction and in a different direction than the double cut guides 504 on the other side of the positioning slot 106.

In additional or alternative embodiments, the double cut guides 504 are positioned on the cutting platform 802 such that there is an angle ($\theta_1$), ($\theta_2$), ($\theta_3$), ($\theta_4$), ($\theta_{x1}$), ($\theta_{x2}$), ($\theta_{x3}$), ($\theta_{x4}$), ($\theta_{y1}$), ($\theta_{y2}$), ($\theta_{y3}$), and ($\theta_{y4}$) created between the double cut guides 504 located on each side of the positioning slot 106, which may be any suitable angle. In various embodiments, the respective angles $\theta_1$), ($\theta_2$), ($\theta_3$), ($\theta_4$), ($\theta_{x1}$), ($\theta_{x2}$), ($\theta_{x3}$), ($\theta_{x4}$), ($\theta_{y1}$), ($\theta_{y2}$), ($\theta_{y3}$), and ($\theta_{y4}$) may each be in the range of about 15° to about 75°.

Figure 9A:
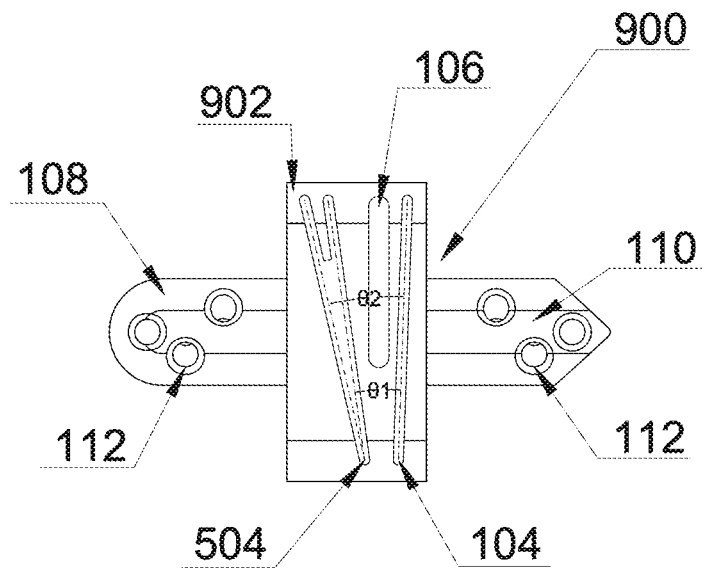
FIG. 9A is diagram illustrating a top view of one embodiment of a surgical cutting block including a single cut guide and a double cut guide.

FIG. 9A is a diagram illustrating one embodiment of a surgical cutting block 900 including a single cut guide 104 and a double cut guide 504. In this embodiment, the single cut guide 104 is positioned/located on a cutting platform 902 on the side of the positioning slot 106 toward the metatarsal fixation platform 110. Further, surgical cutting block 900 includes the double cut guide 504 positioned/located on the cutting platform 902 on the side of the positioning slot 106 toward the cuneiform fixation platform 108.

In some embodiments, the single cut guide 104 and the double cut guide 504 are angled in the same direction (e.g., angled toward the left or toward the right with respect to the user (e.g., a medical professional)). In the illustrated embodiment, the single cut guide 104 and the double cut guide 504 are angled in different directions.

In additional or alternative embodiments, the single cut guide 104 and the double cut guide 504 are positioned on the cutting platform 902 such that there is an angle ($\theta_1$) and ($\theta_2$) created between the single cut guide 104 and the double cut guide 504, which may be any suitable angle. In various embodiments, the respective angles ($\theta_1$) and ($\theta_2$) may each be in the range of about 15° to about 75°.

Figure 9B:
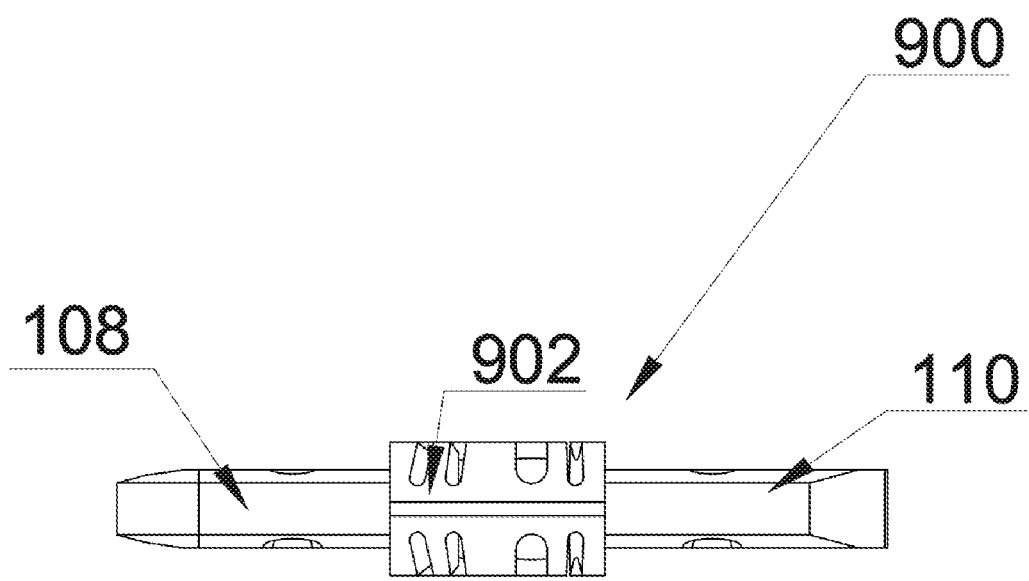
FIG. 9B is diagram illustrating a side profile of the surgical cutting block illustrated in FIG. 9A.

FIG. 9B is diagram illustrating a side profile of the surgical cutting block 900. FIG. 9B illustrates that a single cut guide 104 (e.g., an aperture) and a double cut guide 504 (e.g., an aperture) extend through the cutting platform 902.

Figure 9C:
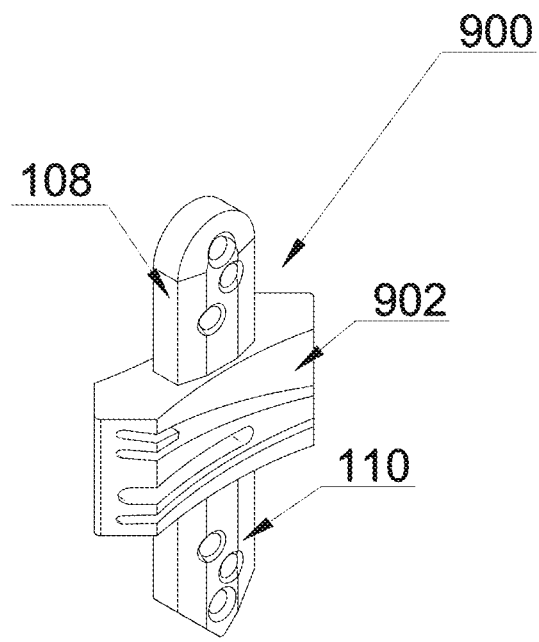
FIG. 9C is a diagram illustrating side view of the surgical cutting block illustrated in FIGS. 9A and 9B.

FIG. 9C is a diagram illustrating side view of the surgical cutting block 900. FIG. 9C illustrates that the cutting platform 902 may include a slope and/or sloped portion that can be any suitable slope included at any suitable portion of the cutting platform.

Figure 10:
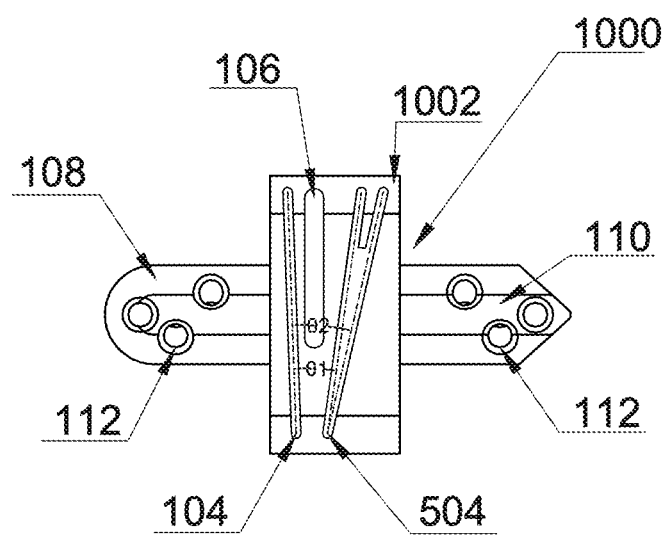
FIG. 10 is a diagram illustrating another embodiment of a surgical cutting block including a single cut guide and a double cut guide.

FIG. 10 is a diagram illustrating another embodiment of a surgical cutting block 1000 including a single cut guide 104 and a double cut guide 504. In this embodiment, the single cut guide 104 is positioned/located on a cutting platform 1002 on the side of the positioning slot 106 toward the cuneiform fixation platform 108. Further, surgical cutting block 1000 includes the double cut guide 504 positioned/located on the cutting platform 1002 on the side of the positioning slot 106 toward the metatarsal fixation platform 110.

In some embodiments, the single cut guide 104 and the double cut guide 504 are angled in the same direction (e.g., angled toward the left or toward the right with respect to the user (e.g., a medical professional)). In the illustrated embodiment, the single cut guide 104 and the double cut guide 504 are angled in different directions.

In additional or alternative embodiments, the single cut guide 104 and the double cut guide 504 are positioned on the cutting platform 102 such that there is an angle ($\theta_1$) and ($\theta_2$) created between the single cut guide 104 and the double cut guide 504, which may be any suitable angle. In various embodiments, the respective angles ($\theta_1$) and ($\theta_2$) may each be in the range of about 15° to about 75°.

Figure 11:
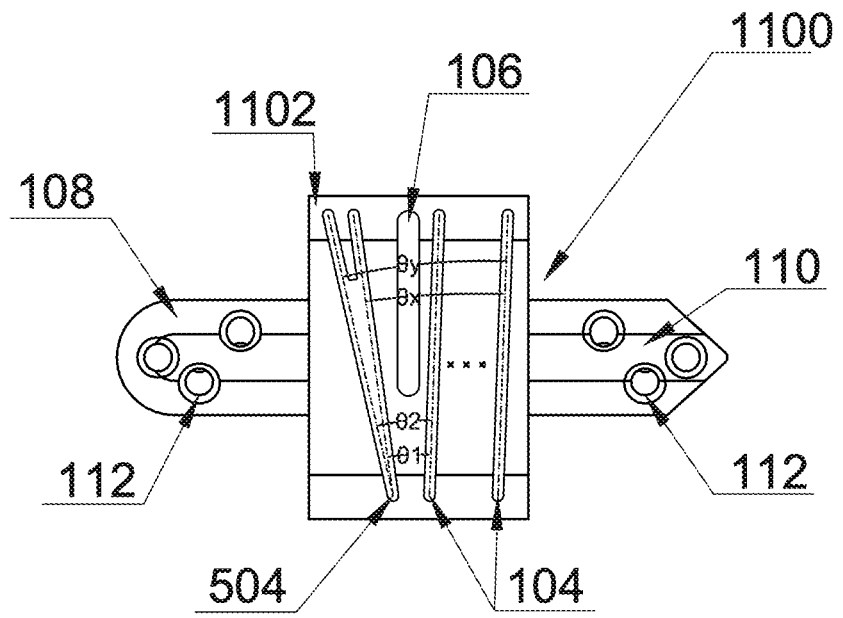
FIG. 11 is a diagram illustrating one embodiment of a surgical cutting block including a plurality of single cut guides and a double cut guide.

FIG. 11 is a diagram illustrating one embodiment of a surgical cutting block 1100 including a plurality of single cut guides 104 and a double cut guide 504. In this embodiment, the plurality of single cut guides 104 are positioned/located on a cutting platform 1102 on the side of the positioning slot 106 toward the metatarsal fixation platform 110. Further, surgical cutting block 1100 includes the double cut guide 504 positioned/located on the cutting platform 1102 on the side of the positioning slot 106 toward the cuneiform fixation platform 108.

In some embodiments, the plurality of single cut guides 104 and the double cut guide 504 are angled in the same direction (e.g., angled toward the left or toward the right with respect to the user (e.g., a medical professional)). In the illustrated embodiment, the plurality of single cut guides 104 and the double cut guide 504 are angled in different directions.

In additional or alternative embodiments, the plurality of single cut guides 104 and the double cut guide 504 are positioned on the cutting platform 1102 such that there is an angle ($\theta_1$), ($\theta_2$), ($\theta_x$), and ($\theta_y$) created between the plurality of single cut guides 104 and the double cut guide 504, which may be any suitable angle. In various embodiments, the respective angles ($\theta_1$), ($\theta_2$), ($\theta_x$), and ($\theta_y$) may each be in the range of about 15° to about 75°.

Figure 12:
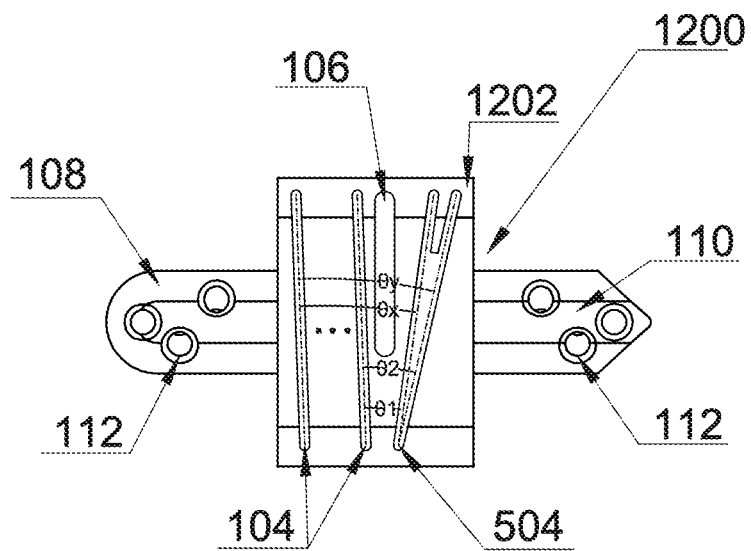
FIG. 12 is a diagram illustrating another embodiment of a surgical cutting block including a plurality of single cut guides and a double cut guide.

FIG. 12 is a diagram illustrating another embodiment of a surgical cutting block including a plurality of single cut guides 104 and a double cut guide 504. In this embodiment, the plurality of single cut guides 104 are positioned/located on a cutting platform 1202 on the side of the positioning slot 106 toward the cuneiform fixation platform 108. Further, surgical cutting block 1200 includes the double cut guide 504 positioned/located on the cutting platform 1202 on the side of the positioning slot 106 toward the metatarsal fixation platform 110.

In some embodiments, the plurality of single cut guides 104 and the double cut guide 504 are angled in the same direction (e.g., angled toward the left or toward the right with respect to the user (e.g., a medical professional)). In the illustrated embodiment, the plurality of single cut guides 104 and the double cut guide 504 are angled in different directions.

In additional or alternative embodiments, the plurality of single cut guides 104 and the double cut guide 504 are positioned on the cutting platform 1202 such that there is an angle ($\theta_1$), ($\theta_2$), ($\theta_x$), and ($\theta_y$) created between the plurality of single cut guides 104 and the double cut guide 504, which may be any suitable angle. In various embodiments, the respective angles ($\theta_1$), ($\theta_2$), ($\theta_x$), and ($\theta_y$) may each be in the range of about 15° to about 75°.

Figure 13:
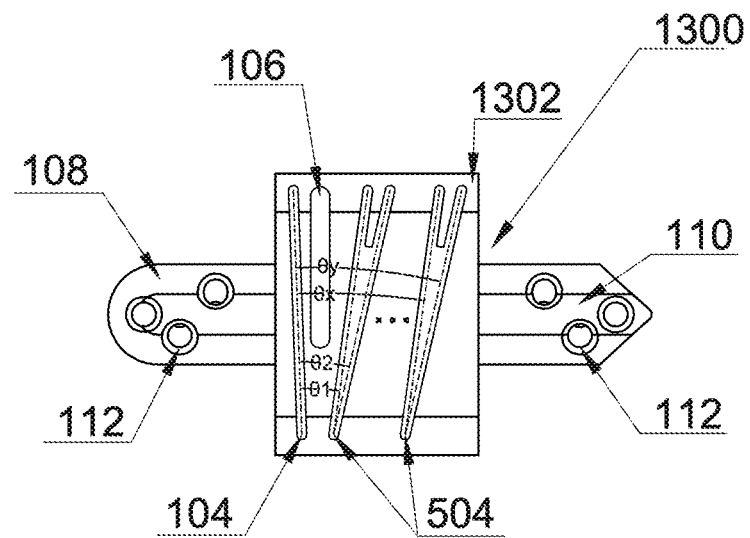
FIG. 13 is a diagram illustrating one embodiment of a surgical cutting block including a plurality of double cut guides and a single cut guide.

FIG. 13 is a diagram illustrating one embodiment of a surgical cutting block 1300 including a plurality of double cut guides 504 and a single cut guide 104. In this embodiment, the plurality of double cut guides 504 are positioned/located on a cutting platform 1302 on the side of the positioning slot 106 toward the metatarsal fixation platform 110. Further, surgical cutting block 1300 includes the single cut guide 104 positioned/located on the cutting platform 1302 on the side of the positioning slot 106 toward the cuneiform fixation platform 108.

In some embodiments, the plurality of double cut guides 504 and the single cut guide 104 are angled in the same direction (e.g., angled toward the left or toward the right with respect to the user (e.g., a medical professional)). In the illustrated embodiment, the plurality of double cut guides 504 and the single cut guide 104 are angled in different directions.

In additional or alternative embodiments, the plurality of double cut guides 504 and the single cut guide 104 are positioned on the cutting platform 1302 such that there is an angle ($\theta_1$), ($\theta_2$), ($\theta_x$), and ($\theta_y$) created between the single cut guide 104 and the plurality of double cut guides 504, which may be any suitable angle. In various embodiments, the respective angles ($\theta_1$), ($\theta_2$), ($\theta_x$), and ($\theta_y$) may each be in the range of about 15° to about 75°.

Figure 14:
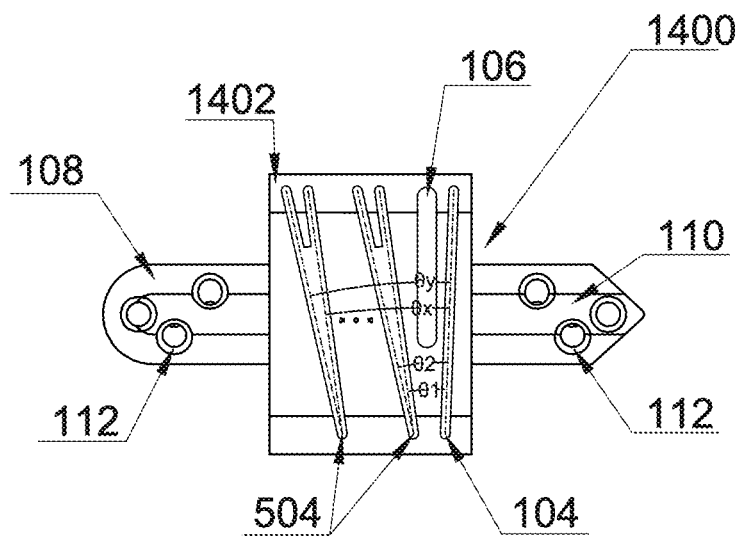
FIG. 14 is a diagram illustrating another embodiment of a surgical cutting block including a plurality of double cut guides and a single cut guide.

FIG. 14 is a diagram illustrating another embodiment of a surgical cutting block 1400 including a plurality of double cut guides 504 and a single cut guide 104. In this embodiment, the plurality of double cut guides 504 are positioned/located on a cutting platform 1402 on the side of the positioning slot 106 toward the cuneiform fixation platform 108. Further, surgical cutting block 1400 includes the single cut guide 104 positioned/located on the cutting platform 1402 on the side of the positioning slot 106 toward the metatarsal fixation platform 110.

In some embodiments, the plurality of double cut guides 504 and the single cut guide 104 are angled in the same direction (e.g., angled toward the left or toward the right with respect to the user (e.g., a medical professional)). In the illustrated embodiment, the plurality of double cut guides 504 and the single cut guide 104 are angled in different directions.

In additional or alternative embodiments, the plurality of double cut guides 504 and the single cut guide 104 are positioned on the cutting platform 1402 such that there is an angle ($\theta_1$), ($\theta_2$), ($\theta_x$), and ($\theta_y$) created between the single cut guide 104 and the plurality of double cut guides 504, which may be any suitable angle. In various embodiments, the respective angles ($\theta_1$), ($\theta_2$), ($\theta_x$), and ($\theta_y$) may each be in the range of about 15° to about 75°.

Figure 15:
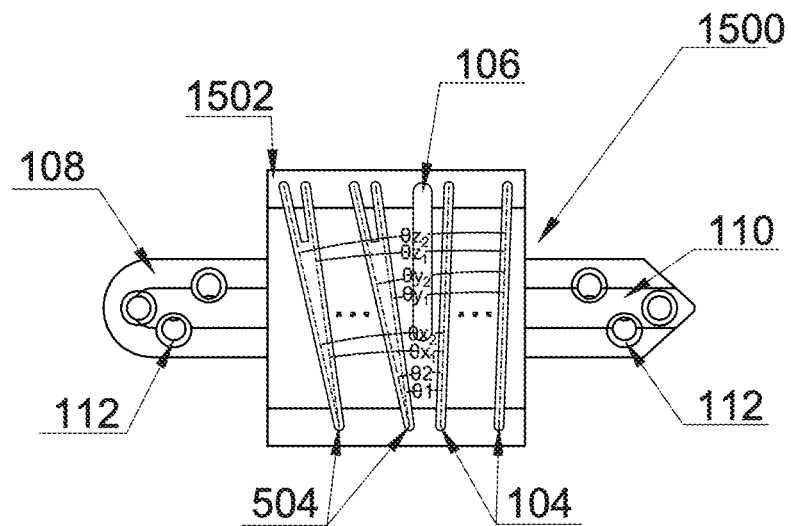
FIG. 15 is a diagram illustrating one embodiment of a surgical cutting block including a plurality of double cut guides and a plurality of single cut guides.

FIG. 15 is a diagram illustrating one embodiment of a surgical cutting block 1500 including a plurality of double cut guides 504 and a plurality of single cut guides 104. In this embodiment, the plurality of double cut guides 504 are located/positioned on a cutting platform 1502 toward the cuneiform fixation platform 108 and the plurality of single cut guides 104 are located/positioned on the cutting platform 1502 toward the metatarsal fixation platform 110.

In some embodiments, the plurality of double cut guides 504 and the plurality of single cut guides 104 are angled in the same direction (e.g., angled toward the left or toward the right with respect to the user (e.g., a medical professional)). In the illustrated embodiment, the plurality of double cut guides 504 and the plurality of single cut guides 104 are angled in different directions.

In additional or alternative embodiments, the plurality of double cut guides 504 and the plurality of single cut guides 104 are positioned on the cutting platform 1402 such that there is an angle ($\theta_1$), ($\theta_2$), ($\theta_{x1}$), ($\theta_{x2}$), ($\theta_{y1}$), ($\theta_{y2}$), ($\theta_{z1}$), and ($\theta_{z2}$) created between the plurality of single cut guides 104 and the plurality of double cut guides 504, which may be any suitable angle. In various embodiments, the respective angles ($\theta_1$), ($\theta_2$), ($\theta_{x1}$), ($\theta_{x2}$), ($\theta_{y1}$), ($\theta_{y2}$), ($\theta_{z1}$), and ($\theta_{z2}$) may each be in the range of about 15° to about 75°.

Figure 16:
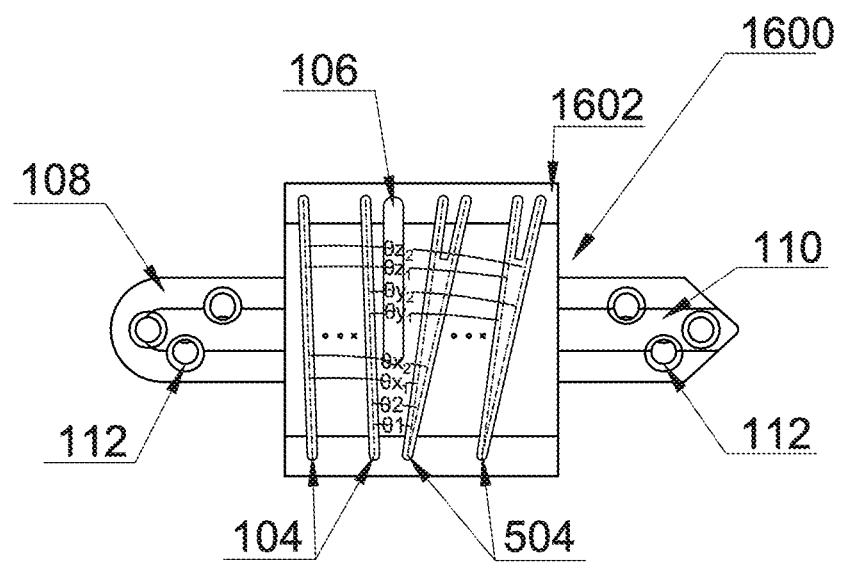
FIG. 16 is a diagram illustrating another embodiment of a surgical cutting block including a plurality of double cut guides and a plurality of single cut guides.

FIG. 16 is a diagram illustrating another embodiment of a surgical cutting block 1600 including a plurality of double cut guides 504 and a plurality of single cut guides 104. In this embodiment, the plurality of double cut guides 504 are located/positioned on a cutting platform 1602 toward the metatarsal fixation platform 110 and the plurality of single cut guides 104 are located/positioned on the cutting platform 1602 toward the cuneiform fixation platform 108.

In some embodiments, the plurality of double cut guides 504 and the plurality of single cut guides 104 are angled in the same direction (e.g., angled toward the left or toward the right with respect to the user (e.g., a medical professional)). In the illustrated embodiment, the plurality of double cut guides 504 and the plurality of single cut guides 104 are angled in different directions.

In additional or alternative embodiments, the plurality of double cut guides 504 and the plurality of single cut guides 104 are positioned on the cutting platform 1402 such that there is an angle ($\theta_1$), ($\theta_2$), ($\theta_{x1}$), ($\theta_{x2}$), ($\theta_{y1}$), ($\theta_{y2}$), ($\theta_{z1}$), and ($\theta_{z2}$) created between the plurality of single cut guides 104 and the plurality of double cut guides 504, which may be any suitable angle. In various embodiments, the respective angles ($\theta_1$), ($\theta_2$), ($\theta_{x1}$), ($\theta_{x2}$), ($\theta_{y1}$), ($\theta_{y2}$), ($\theta_{z1}$), and ($\theta_{z2}$) may each be in the range of about 15° to about 75°.

Figure 17:
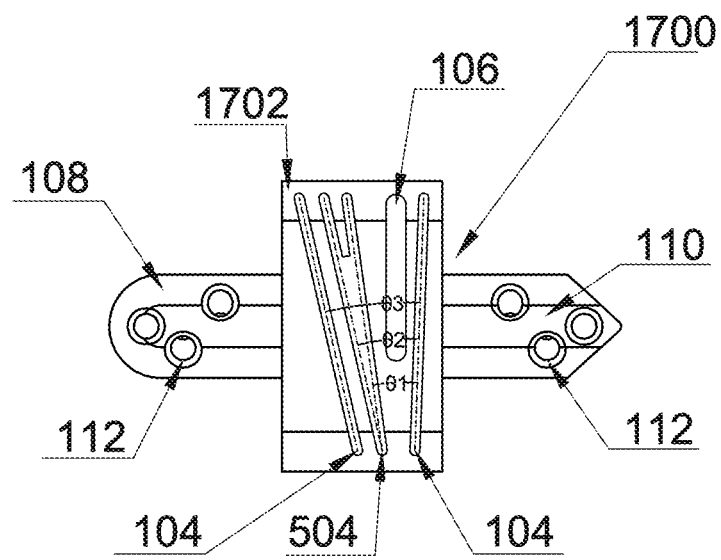
FIG. 17 is a diagram illustrating one embodiment of a surgical cutting block including a double cut guide and a plurality of single cut guides.

FIG. 17 is a diagram illustrating one embodiment of a surgical cutting block 1700 including a double cut guide 504 and a plurality of single cut guides 104. In this embodiment, the double cut guide 504 and one single cut guide 104 are located/positioned on a cutting platform 1702 toward the cuneiform fixation platform 108 and one single cut guide 104 is located/positioned on the cutting platform 1702 toward the metatarsal fixation platform 110. Further, the double cut guide 504 is located/positioned to the right of the single cut guide 104 on the cuneiform fixation platform 108 side of the cutting platform 102.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the single cut guide 104 on the opposite side of the positioning slot 106 is angled in a different direction.

In additional or alternative embodiments, the double cut guide 504 and the single cut guide 104 are positioned on the cutting platform 1402 such that there is an angle ($\theta_1$), ($\theta_2$), and ($\theta_3$) created between the double cut guide 504 and the single cut guide 104 and the other single cut guide 104, which may be any suitable angle. In various embodiments, the respective angles ($\theta_1$), ($\theta_2$), and ($\theta_3$) may each be in the range of about 15° to about 75°.

Figure 18:
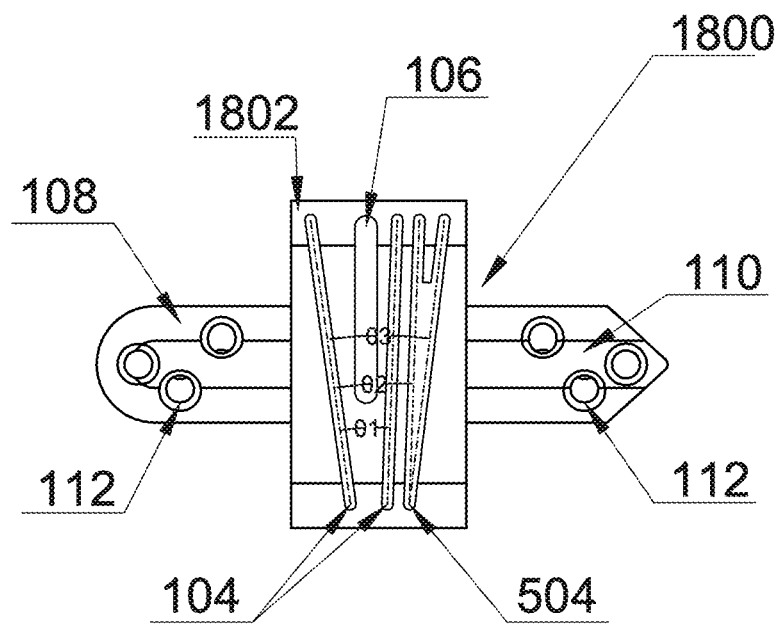
FIG. 18 is a diagram illustrating another embodiment of a surgical cutting block including a double cut guide and a plurality of single cut guides.

FIG. 18 is a diagram illustrating another embodiment of a surgical cutting block 1800 including a double cut guide 504 and a plurality of single cut guides 104. In this embodiment, the double cut guide 504 and one single cut guide 104 are located/positioned on a cutting platform 1802 toward the metatarsal fixation platform 110 and one single cut guide 104 is located/positioned on the cutting platform 1802 toward the cuneiform fixation platform 108. Further, the double cut guide 504 is located/positioned to the right of the single cut guide 104 on the metatarsal fixation platform 110 side of the cutting platform 1802.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the single cut guide 104 on the opposite side of the positioning slot 106 is angled in a different direction.

In additional or alternative embodiments, the double cut guide 504 and the single cut guide 104 are positioned on the cutting platform 1402 such that there is an angle ($\theta_1$), ($\theta_2$), and ($\theta_3$) created between the double cut guide 504 and the single cut guide 104 and the other single cut guide 104, which may be any suitable angle. In various embodiments, the respective angles ($\theta_1$), ($\theta_2$), and ($\theta_3$) may each be in the range of about 15° to about 75°.

Figure 19:
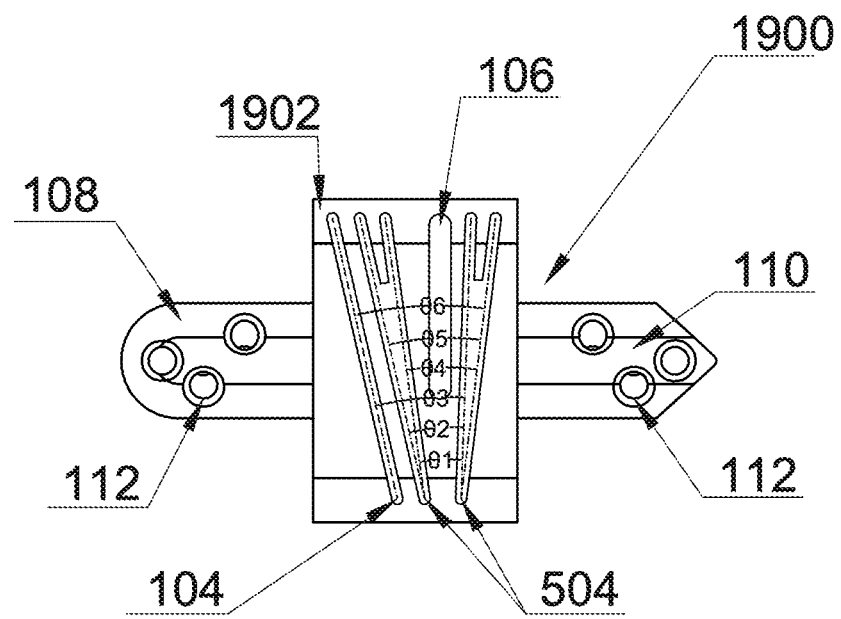
FIG. 19 is a diagram illustrating one embodiment of a surgical cutting block including a plurality of double cut guides and a single cut guide.

FIG. 19 is a diagram illustrating one embodiment of a surgical cutting block 1900 including a plurality of double cut guides 504 and a single cut guide 104. In this embodiment, one double cut guide 504 and the single cut guide 104 are located/positioned on a cutting platform 1902 toward the cuneiform fixation platform 108 and one double cut guide 504 is located/positioned on the cutting platform 1902 toward the metatarsal fixation platform 110. Further, the double cut guide 504 is located/positioned to the right of the single cut guide 104 on the cuneiform fixation platform 108 side of the cutting platform 1902.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the double cut guide 504 on the opposite side of the positioning slot 106 is angled in a different direction.

In additional or alternative embodiments, the double cut guide 504 and the single cut guide 104 are positioned on the cutting platform 1402 such that there is an angle ($\theta_1$), ($\theta_2$), ($\theta_3$), ($\theta_4$), ($\theta_5$), and ($\theta_6$) created between the double cut guide 504 and the single cut guide 104 and the other double cut guide 504, which may be any suitable angle. In various embodiments, the respective angles ($\theta_1$), ($\theta_2$), ($\theta_3$), ($\theta_4$), ($\theta_5$), and ($\theta_6$) may each be in the range of about 15° to about 75°.

Figure 20:
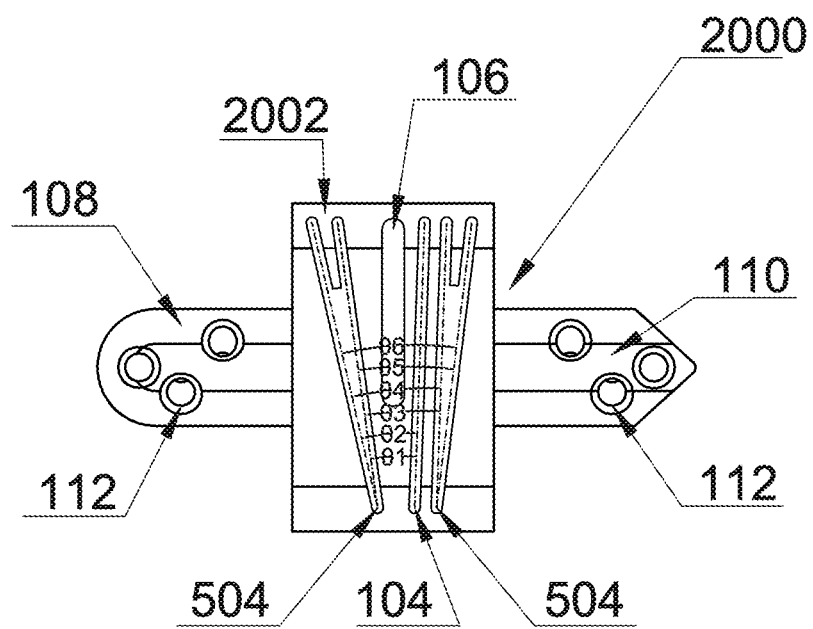
FIG. 20 is a diagram illustrating another embodiment of a surgical cutting block including a plurality of double cut guides and a single cut guide.

FIG. 20 is a diagram illustrating another embodiment of a surgical cutting block 2000 including a plurality of double cut guides 504 and a single cut guide 104. In this embodiment, one double cut guide 504 and the single cut guide 104 are located/positioned on a cutting platform 2002 toward the metatarsal fixation platform 110 and one double cut guide 504 is located/positioned on the cutting platform 2002 toward the cuneiform fixation platform 108. Further, the double cut guide 504 is located/positioned to the right of the single cut guide 104 on the metatarsal fixation platform 110 side of the cutting platform 2002.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the double cut guide 504 on the opposite side of the positioning slot 106 is angled in a different direction.

In additional or alternative embodiments, the double cut guide 504 and the single cut guide 104 are positioned on the cutting platform 1402 such that there is an angle $(\theta_1)$, $(\theta_2)$, $(\theta_3)$, $(\theta_4)$, $(\theta_5)$, and $(\theta_6)$ created between the double cut guide 504 and the single cut guide 104 and the other double cut guide 504, which may be any suitable angle. In various embodiments, the respective angles $(\theta_1)$, $(\theta_2)$, $(\theta_3)$, $(\theta_4)$, $(\theta_5)$, and $(\theta_6)$ may each be in the range of about 15° to about 75°.

Figure 21:
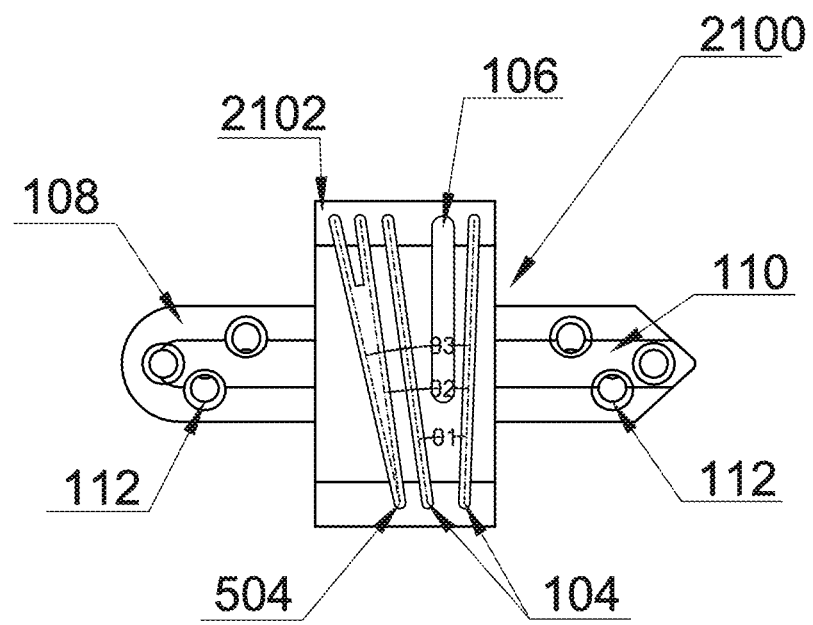
FIG. 21 is a diagram illustrating one embodiment of a surgical cutting block including a double cut guide and a plurality of single cut guides.

FIG. 21 is a diagram illustrating one embodiment of a surgical cutting block 2100 including a double cut guide 504 and a plurality of single cut guides 104. In this embodiment, the double cut guide 504 and one single cut guide 104 are located/positioned on a cutting platform 2102 toward the cuneiform fixation platform 108 and one single cut guide 104 is located/positioned on the cutting platform 2102 toward the metatarsal fixation platform 110. Further, the double cut guide 504 is located/positioned to the left of the single cut guide 104 on the cuneiform fixation platform 108 side of the cutting platform 2102.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the single cut guide 104 on the opposite side of the positioning slot 106 is angled in a different direction.

In additional or alternative embodiments, the double cut guide 504 and the single cut guide 104 are positioned on the cutting platform 1402 such that there is an angle $(\theta_1)$, $(\theta_2)$, and $(\theta_3)$ created between the double cut guide 504 and the single cut guide 104 and the other single cut guide 104, which may be any suitable angle. In various embodiments, the respective angles $(\theta_1)$, $(\theta_2)$, and $(\theta_3)$ may each be in the range of about 15° to about 75°.

Figure 22:
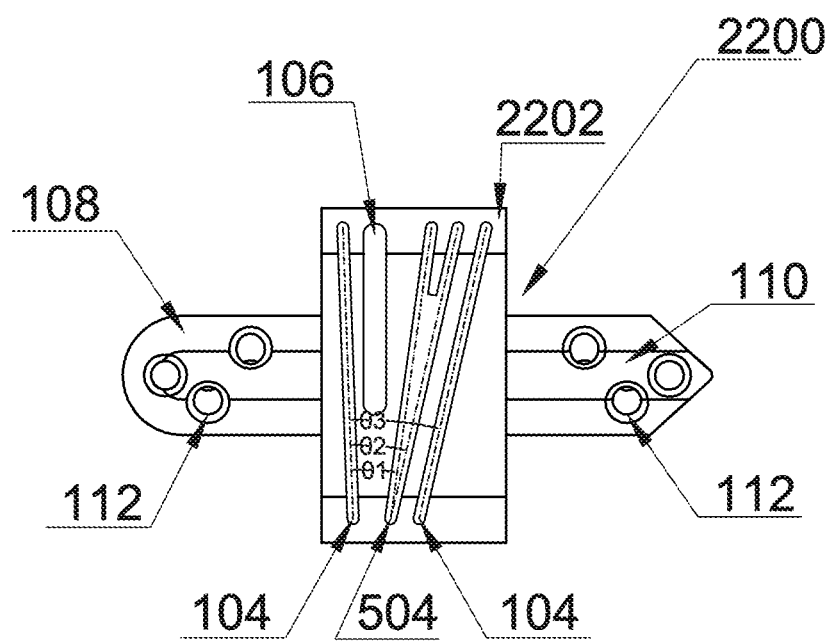
FIG. 22 is a diagram illustrating another embodiment of a surgical cutting block including a double cut guide and a plurality of single cut guides.

FIG. 22 is a diagram illustrating another embodiment of a surgical cutting block 2200 including a double cut guide 504 and a plurality of single cut guides 104. In this embodiment, the double cut guide 504 and one single cut guide 104 are located/positioned on a cutting platform 2202 toward the metatarsal fixation platform 110 and one single cut guide 104 is located/positioned on the cutting platform 2202 toward the cuneiform fixation platform 108. Further, the double cut guide 504 is located/positioned to the left of the single cut guide 104 on the metatarsal fixation platform 110 side of the cutting platform 2202.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the single cut guide 104 on the opposite side of the positioning slot 106 is angled in a different direction.

In additional or alternative embodiments, the double cut guide 504 and the single cut guide 104 are positioned on the cutting platform 1402 such that there is an angle $(\theta_1)$, $(\theta_2)$, and $(\theta_3)$ created between the double cut guide 504 and the single cut guide 104 and the other single cut guide 104, which may be any suitable angle. In various embodiments, the respective angles $(\theta_1)$, $(\theta_2)$, and $(\theta_3)$ may each be in the range of about 15° to about 75°.

Figure 23:
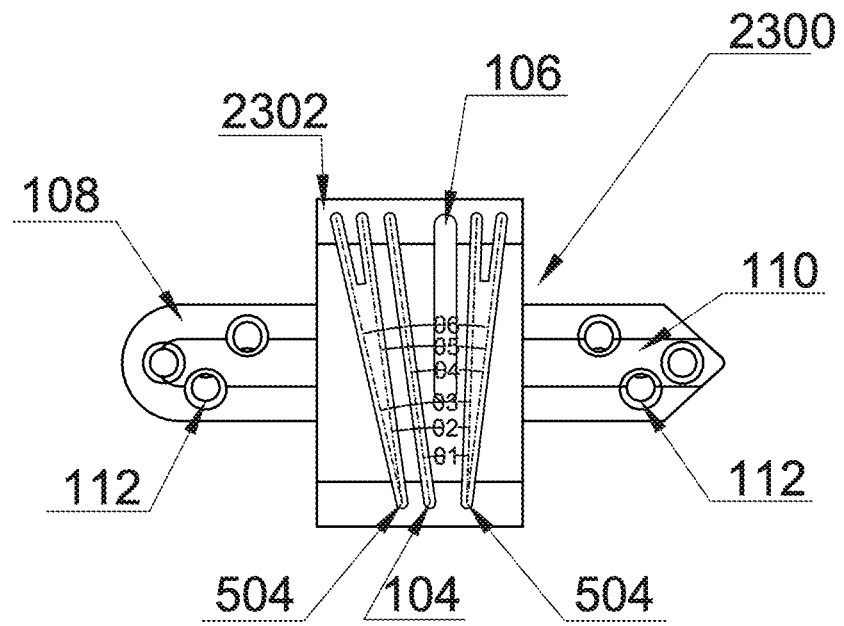
FIG. 23 is a diagram illustrating an embodiment of a surgical cutting block including a plurality of double cut guides and a single cut guide.

FIG. 23 is a diagram illustrating one embodiment of a surgical cutting block 2300 including a plurality of double cut guides 504 and a single cut guide 104. In this embodiment, one double cut guide 504 and the single cut guide 104 are located/positioned on a cutting platform 2302 toward the cuneiform fixation platform 108 and one double cut guide 504 is located/positioned on the cutting platform 2302 toward the metatarsal fixation platform 110. Further, the double cut guide 504 is located/positioned to the left of the single cut guide 104 on the cuneiform fixation platform 108 side of the cutting platform 2302.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the double cut guide 504 on the opposite side of the positioning slot 106 is angled in a different direction.

In additional or alternative embodiments, the double cut guide 504 and the single cut guide 104 are positioned on the cutting platform 1402 such that there is an angle $(\theta_1)$, $(\theta_2)$, $(\theta_3)$, $(\theta_4)$, $(\theta_5)$, and $(\theta_6)$ created between the double cut guide 504 and the single cut guide 104 and the other double cut guide 504, which may be any suitable angle. In various embodiments, the respective angles $(\theta_1)$, $(\theta_2)$, $(\theta_3)$, $(\theta_4)$, $(\theta_5)$, and $(\theta_6)$ may each be in the range of about 15° to about 75°.

Figure 24:
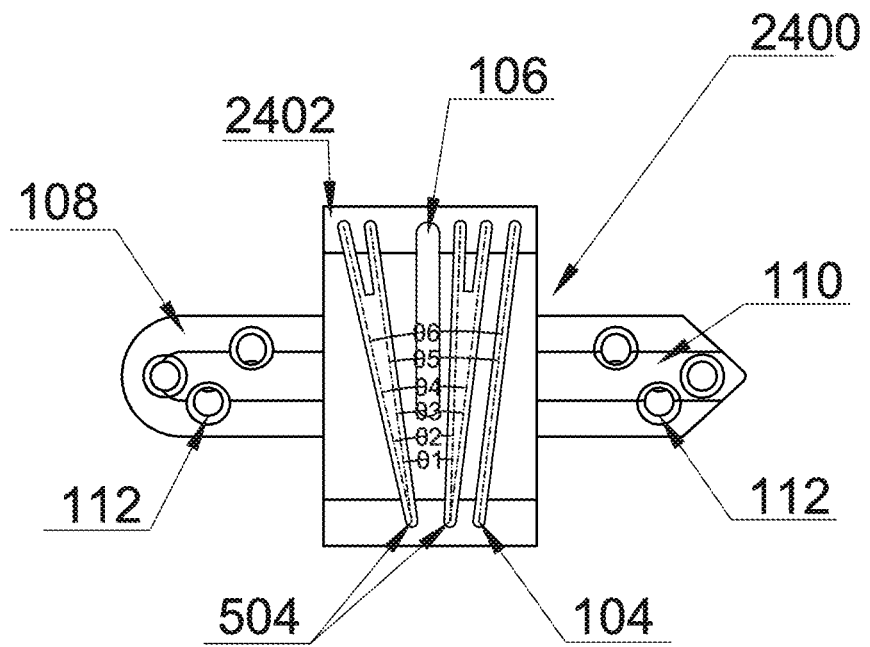
FIG. 24 is a diagram illustrating another embodiment of a surgical cutting block including a plurality of double cut guides and a single cut guide.

FIG. 24 is a diagram illustrating another embodiment of a surgical cutting block 2400 including a plurality of double cut guides 504 and a single cut guide 104. In this embodiment, one double cut guide 504 and the single cut guide 104 are located/positioned on a cutting platform 2402 toward the metatarsal fixation platform 110 and one double cut guide 504 is located/positioned on the cutting platform 2402 toward the cuneiform fixation platform 108. Further, the double cut guide 504 is located/positioned to the left of the single cut guide 104 on the metatarsal fixation platform 110 side of the cutting platform 2402.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the double cut guide 504 on the opposite side of the positioning slot 106 is angled in a different direction.

In additional or alternative embodiments, the double cut guide 504 and the single cut guide 104 are positioned on the cutting platform 1402 such that there is an angle $(\theta_1)$, $(\theta_2)$, $(\theta_3)$, $(\theta_4)$, $(\theta_5)$, and $(\theta_6)$ created between the double cut guide 504 and the single cut guide 104 and the other double cut guide 504, which may be any suitable angle. In various embodiments, the respective angles $(\theta_1)$, $(\theta_2)$, $(\theta_3)$, $(\theta_4)$, $(\theta_5)$, and $(\theta_6)$ may each be in the range of about 15° to about 75°.

Figure 25:
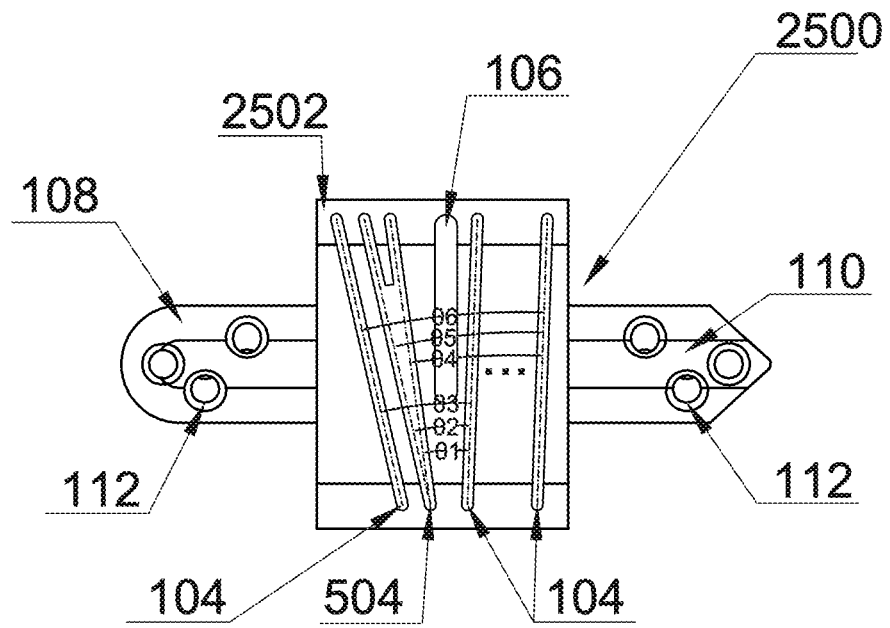
FIG. 25 is a diagram illustrating another embodiment of a surgical cutting block including a double cut guide and a plurality of single cut guides.

FIG. 25 is a diagram illustrating another embodiment of a surgical cutting block 2500 including a double cut guide 504 and a plurality of single cut guides 104. In this embodiment, the double cut guide 504 and one single cut guide 104 are located/positioned on a cutting platform 2502 toward the cuneiform fixation platform 108 and a plurality of single cut guides 104 are located/positioned on the cutting platform 2502 toward the metatarsal fixation platform 110. Further, the double cut guide 504 is located/positioned to the right of the single cut guide 104 on the cuneiform fixation platform 108 side of the cutting platform 2502.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the plurality of single cut guides 104 on the opposite side of the positioning slot 106 are angled in the direction as one another and a different direction than the double cut guide 504 and the single cut guide 104.

In additional or alternative embodiments, the double cut guide 504 and the single cut guide 104 are positioned on the cutting platform 1402 such that there is an angle ($\theta_1$), ($\theta_2$), ($\theta_3$), ($\theta_4$), ($\theta_5$), and ($\theta_6$) created between the double cut guide 504 and the single cut guide 104 and the other plurality of single cut guides 104, which may be any suitable angle. In various embodiments, the respective angles ($\theta_1$), ($\theta_2$), ($\theta_3$), ($\theta_4$), ($\theta_5$), and ($\theta_6$) may each be in the range of about 15° to about 75°.

Figure 26:
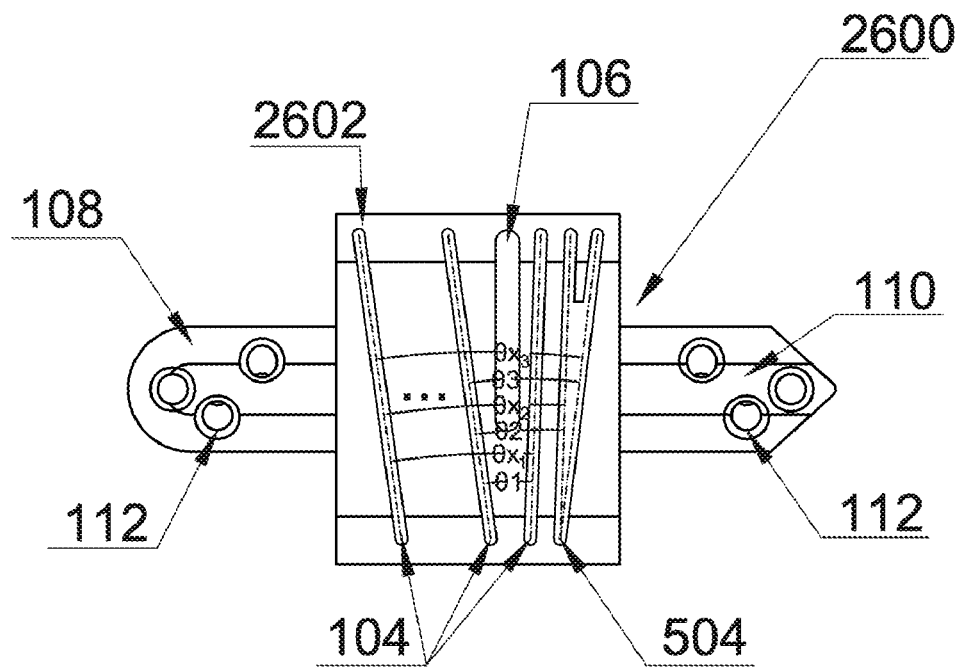
FIG. 26 is a diagram illustrating still another embodiment of a surgical cutting block including a double cut guide and a plurality of single cut guides.

FIG. 26 is a diagram illustrating another embodiment of a surgical cutting block 2600 including a double cut guide 504 and a plurality of single cut guides 104. In this embodiment, the double cut guide 504 and one single cut guide 104 are located/positioned on a cutting platform 2602 toward the metatarsal fixation platform 110 and a plurality of single cut guides 104 are located/positioned on the cutting platform 2602 toward the cuneiform fixation platform 108. Further, the double cut guide 504 is located/positioned to the right of the single cut guide 104 on the metatarsal fixation platform 110 side of the cutting platform 2602.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction, the plurality of single cut guides 104 on the opposite side of the positioning slot 106 are angled in the direction as one another and a different direction than the double cut guide 504 and the single cut guide 104.

In additional or alternative embodiments, the double cut guide 504 and the single cut guide 104 are positioned on the cutting platform 1402 such that there is an angle ($\theta_1$), ($\theta_2$), ($\theta_3$), ($\theta_{x1}$), ($\theta_{x2}$), and ($\theta_{x3}$) created between the double cut guide 504 and the single cut guide 104 and the other plurality of single cut guides 104, which may be any suitable angle. In various embodiments, the respective angles ($\theta_1$), ($\theta_2$), ($\theta_3$), ($\theta_{x1}$), ($\theta_{x2}$), and ($\theta_{x3}$) may each be in the range of about 15° to about 75°.

Figure 27:
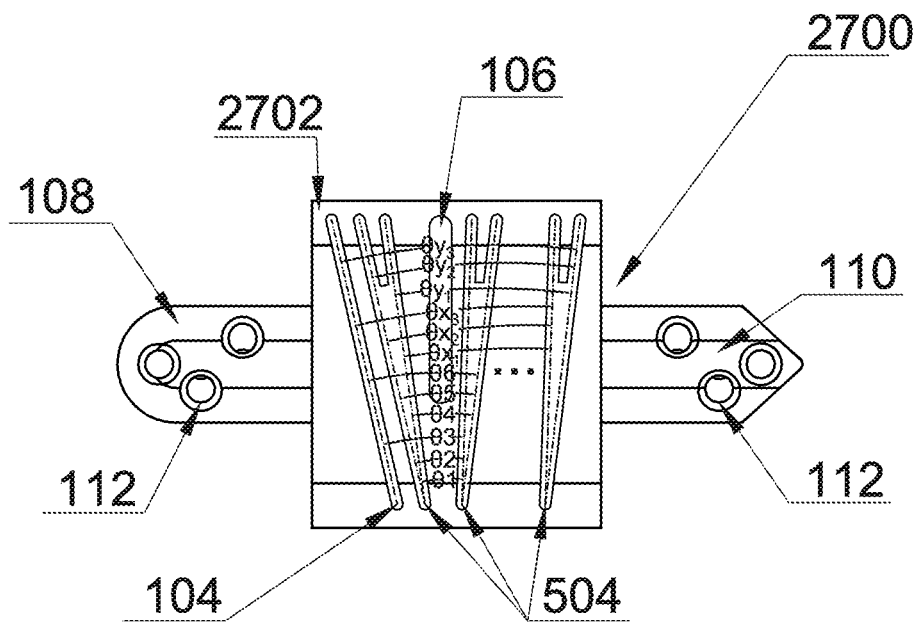
FIG. 27 is a diagram illustrating another embodiment of a surgical cutting block including a plurality of double cut guides and a single cut guide.

FIG. 27 is a diagram illustrating one embodiment of a surgical cutting block 2700 including a plurality of double cut guides 504 and a single cut guide 104. In this embodiment, one double cut guide 504 and the single cut guide 104 are located/positioned on a cutting platform 2702 toward the cuneiform fixation platform 108 and a plurality of double cut guides 504 are located/positioned on the cutting platform 2702 toward the metatarsal fixation platform 110. Further, the double cut guide 504 is located/positioned to the right of the single cut guide 104 on the cuneiform fixation platform 108 side of the cutting platform 2702.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the plurality of double cut guides 504 on the opposite side of the positioning slot 106 are angled in a different direction.

In additional or alternative embodiments, the double cut guide 504 and the single cut guide 104 are positioned on the cutting platform 1402 such that there is an angle ($\theta_1$), ($\theta_2$), ($\theta_3$), ($\theta_4$), ($\theta_5$), ($\theta_6$), ($\theta_{x1}$), ($\theta_{x2}$), ($\theta_{x3}$), ($\theta_{y1}$), ($\theta_{y2}$), and ($\theta_{y3}$) created between the double cut guide 504 and the single cut guide 104 and the plurality of double cut guides 504, which may be any suitable angle. In various embodiments, the respective angles ($\theta_1$), ($\theta_2$), ($\theta_3$), ($\theta_4$), ($\theta_5$), ($\theta_6$), ($\theta_{x1}$), ($\theta_{x2}$), ($\theta_{x3}$), ($\theta_{y1}$), ($\theta_{y2}$), and ($\theta_{y3}$) may each be in the range of about 15° to about 75°.

Figure 28:
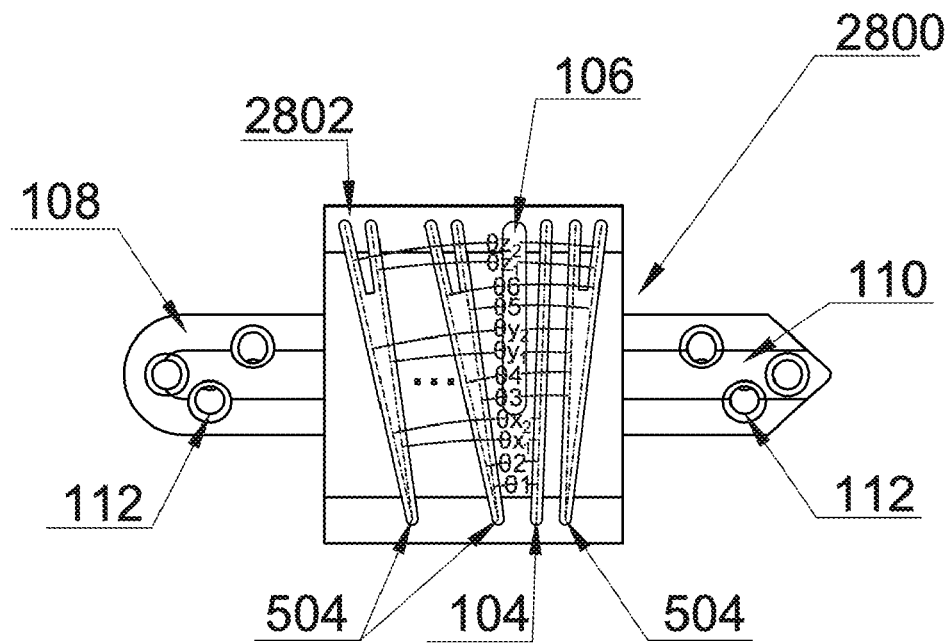
FIG. 28 is a diagram illustrating still another embodiment of a surgical cutting block including a plurality of double cut guides and a single cut guide.

FIG. 28 is a diagram illustrating another embodiment of a surgical cutting block 2800 including a plurality of double cut guides 504 and a single cut guide 104. In this embodiment, one double cut guide 504 and the single cut guide 104 are located/positioned on a cutting platform 2802 toward the metatarsal fixation platform 110 and a plurality of double cut guides 504 are located/positioned on the cutting platform 2802 toward the cuneiform fixation platform 108. Further, the double cut guide 504 is located/positioned to the right of the single cut guide 104 on the metatarsal fixation platform 110 side of the cutting platform 2802.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the plurality of double cut guides 504 on the opposite side of the positioning slot 106 are angled in a different direction.

In additional or alternative embodiments, the double cut guide 504 and the single cut guide 104 are positioned on the cutting platform 1402 such that there is an angle ($\theta_1$), ($\theta_2$), ($\theta_3$), ($\theta_4$), ($\theta_5$), ($\theta_6$), ($\theta_{x1}$), ($\theta_{x2}$), ($\theta_{y1}$), ($\theta_{y2}$), ($\theta_{z1}$), and ($\theta_{z2}$) created between the double cut guide 504 and the single cut guide 104 and the plurality of double cut guides 504, which may be any suitable angle. In various embodiments, the respective angles ($\theta_1$), ($\theta_2$), ($\theta_3$), ($\theta_4$), ($\theta_5$), ($\theta_6$), ($\theta_{x1}$), ($\theta_{x2}$), ($\theta_{y1}$), ($\theta_{y1}$), ($\theta_{z1}$), and ($\theta_{z2}$) may each be in the range of about 15° to about 75°.

Figure 29:
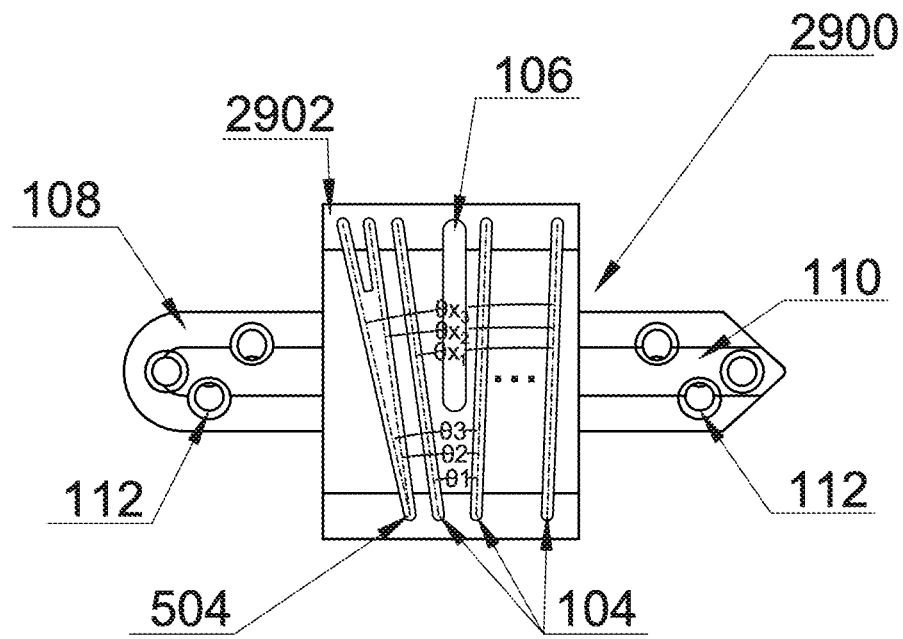
FIG. 29 is a diagram illustrating another embodiment of a surgical cutting block including a double cut guide and a plurality of single cut guides.

FIG. 29 is a diagram illustrating another embodiment of a surgical cutting block 2900 including a double cut guide 504 and a plurality of single cut guides 104. In this embodiment, the double cut guide 504 and one single cut guide 104 are located/positioned on a cutting platform 2902 toward the cuneiform fixation platform 108 and a plurality of single cut guides 104 are located/positioned on the cutting platform 2902 toward the metatarsal fixation platform 110. Further, the double cut guide 504 is located/positioned to the left of the single cut guide 104 on the cuneiform fixation platform 108 side of the cutting platform 2902.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction, the plurality of single cut guides 104 on the opposite side of the positioning slot 106 are angled in the direction as one another and a different direction than the double cut guide 504 and the single cut guide 104.

In additional or alternative embodiments, the double cut guide 504 and the single cut guide 104 are positioned on the cutting platform 1402 such that there is an angle ($\theta_1$), ($\theta_2$), ($\theta_3$), ($\theta_{x1}$), ($\theta_{x2}$), and ($\theta_{x3}$) created between the double cut guide 504 and the single cut guide 104 and the other plurality of single cut guides 104, which may be any suitable angle. In various embodiments, the respective angles ($\theta_1$), ($\theta_2$), ($\theta_3$), ($\theta_{x1}$), ($\theta_{x2}$), and ($\theta_{x3}$) may each be in the range of about 15° to about 75°.

Figure 30:
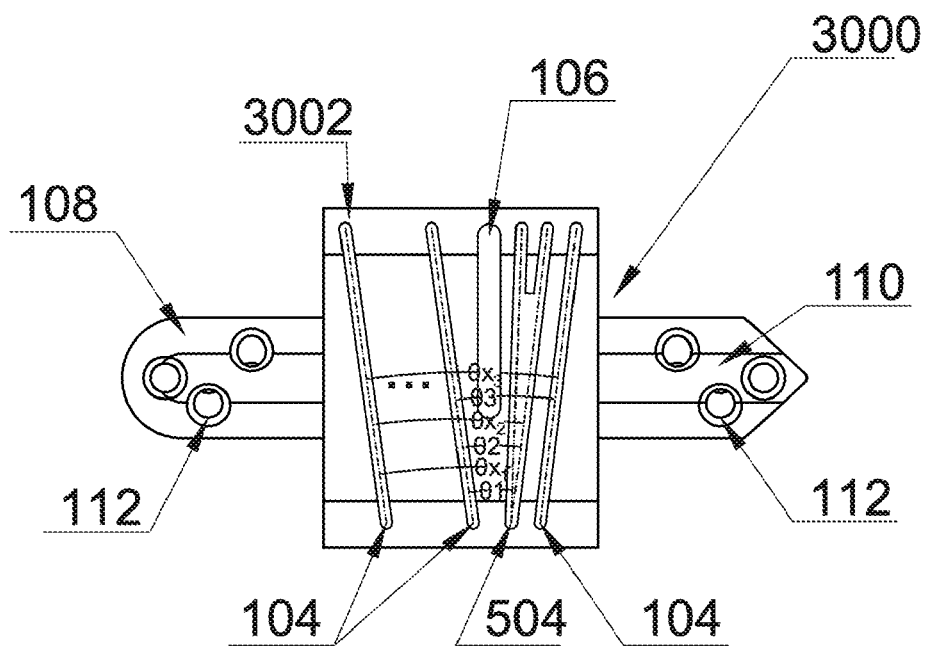
FIG. 30 is a diagram illustrating still another embodiment of a surgical cutting block including a double cut guide and a plurality of single cut guides.

FIG. 30 is a diagram illustrating another embodiment of a surgical cutting block 3000 including a double cut guide 504 and a plurality of single cut guides 104. In this embodiment, the double cut guide 504 and one single cut guide 104 are located/positioned on a cutting platform 3002 toward the metatarsal fixation platform 110 and a plurality of single cut guides 104 are located/positioned on the cutting platform 3002 toward the cuneiform fixation platform 108. Further, the double cut guide 504 is located/positioned to the left of the single cut guide 104 on the metatarsal fixation platform 110 side of the cutting platform 3002.

In some embodiments, the double cut guide 504 and the single cut guides 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction, the plurality of single cut guides 104 on the opposite side of the positioning slot 106 are angled in the direction as one another and a different direction than the double cut guide 504 and the single cut guide 104.

In additional or alternative embodiments, the double cut guide 504 and the single cut guide 104 are positioned on the cutting platform 1402 such that there is an angle ($\theta_1$), ($\theta_2$), ($\theta_3$), ($\theta_{x1}$), ($\theta_{x2}$), and ($\theta_{x3}$) created between the double cut guide 504 and the single cut guide 104 and the other plurality of single cut guides 104, which may be any suitable angle. In various embodiments, the respective angles ($\theta_1$), ($\theta_2$), ($\theta_3$), ($\theta_{x1}$), ($\theta_{x2}$), and ($\theta_{x3}$) may each be in the range of about 15° to about 75°.

Figure 31:
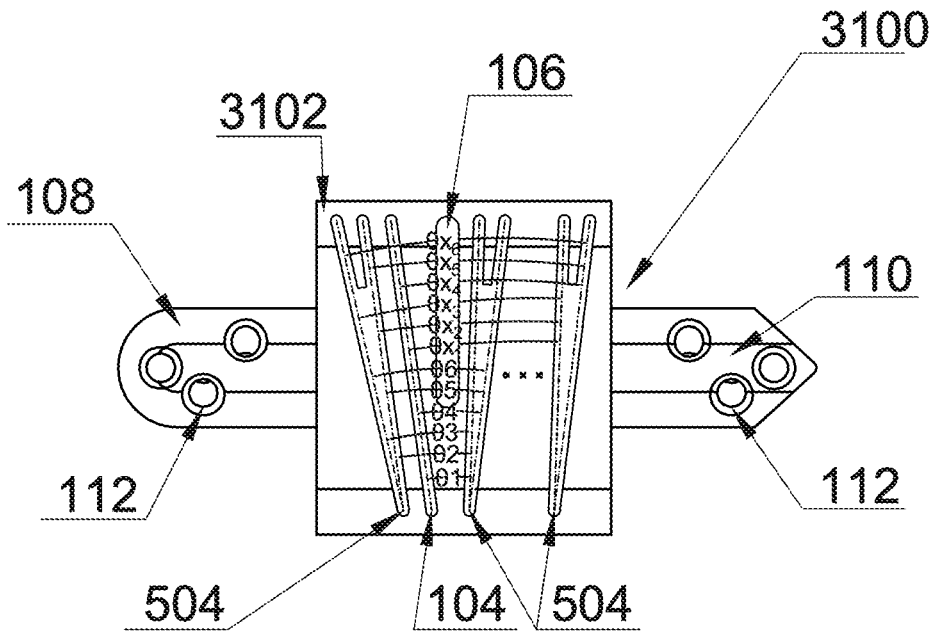
FIG. 31 is a diagram illustrating another embodiment of a surgical cutting block including a plurality of double cut guides and a single cut guide.

FIG. 31 is a diagram illustrating one embodiment of a surgical cutting block 3100 including a plurality of double cut guides 504 and a single cut guide 104. In this embodiment, one double cut guide 504 and the single cut guide 104 are located/positioned on a cutting platform 3102 toward the cuneiform fixation platform 108 and a plurality of double cut guides 504 are located/positioned on the cutting platform 3102 toward the metatarsal fixation platform 110. Further, the double cut guide 504 is located/positioned to the left of the single cut guide 104 on the cuneiform fixation platform 108 side of the cutting platform 3102.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the plurality of double cut guides 504 on the opposite side of the positioning slot 106 are angled in a different direction.

In additional or alternative embodiments, the double cut guide 504 and the single cut guide 104 are positioned on the cutting platform 1402 such that there is an angle ($\theta_1$), ($\theta_2$), ($\theta_3$), ($\theta_4$), ($\theta_5$), ($\theta_6$), ($\theta_{x1}$), ($\theta_{x2}$), ($\theta_{x3}$), ($\theta_{x4}$), ($\theta_{x5}$), and ($\theta_{x6}$) created between the double cut guide 504 and the single cut guide 104 and the plurality of double cut guides 504, which may be any suitable angle. In various embodiments, the respective angles ($\theta_1$), ($\theta_2$), ($\theta_3$), ($\theta_4$), ($\theta_5$), ($\theta_6$), (NO, ($\theta_{x2}$), ($\theta_{x3}$), ($\theta_{x4}$), ($\theta_{x5}$), and ($\theta_{x6}$) may each be in the range of about 15° to about 75°.

Figure 32:
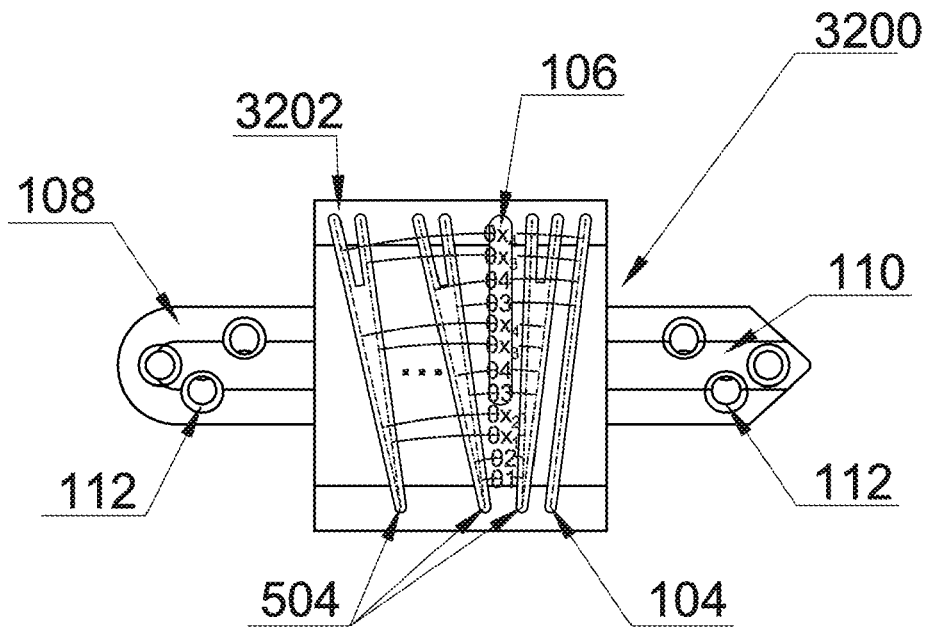
FIG. 32 is a diagram illustrating still another embodiment of a surgical cutting block including a plurality of double cut guides and a single cut guide.

FIG. 32 is a diagram illustrating another embodiment of a surgical cutting block 3200 including a plurality of double cut guides 504 and a single cut guide 104. In this embodiment, one double cut guide 504 and the single cut guide 104 are located/positioned on a cutting platform 3202 toward the metatarsal fixation platform 110 and a plurality of double cut guides 504 are located/positioned on the cutting platform 3202 toward the cuneiform fixation platform 108. Further, the double cut guide 504 is located/positioned to the left of the single cut guide 104 on the metatarsal fixation platform 110 side of the cutting platform 3202.

In some embodiments, the double cut guides 504 and the single cut guide 104 are angled in the same direction (e.g., angled toward the left or toward the right with respect to the user (e.g., a medical professional)). In the illustrated embodiment, the double cut guide 504 and the single cut guide 104 on the same side of the positioning slot 106 are angled in the same direction and the plurality of double cut guides 504 on the opposite side of the positioning slot 106 are angled in a different direction.

In additional or alternative embodiments, the double cut guide 504 and the single cut guide 104 are positioned on the cutting platform 1402 such that there is an angle ($\theta_1$), ($\theta_2$), ($\theta_3$), ($\theta_4$), ($\theta_5$), ($\theta_6$), ($\theta_{x1}$), ($\theta_{x2}$), ($\theta_{x3}$), ($\theta_{x4}$), ($\theta_{x5}$), and ($\theta_{x6}$) created between the double cut guide 504 and the single cut guide 104 and the plurality of double cut guides 504, which may be any suitable angle. In various embodiments, the respective angles ($\theta_1$), ($\theta_2$), ($\theta_3$), ($\theta_4$), ($\theta_5$), ($\theta_6$), (NO, ($\theta_{x2}$), ($\theta_{x3}$), ($\theta_{x4}$), ($\theta_{x5}$), and ($\theta_{x6}$) may each be in the range of about 15° to about 75°.

Figure 33:
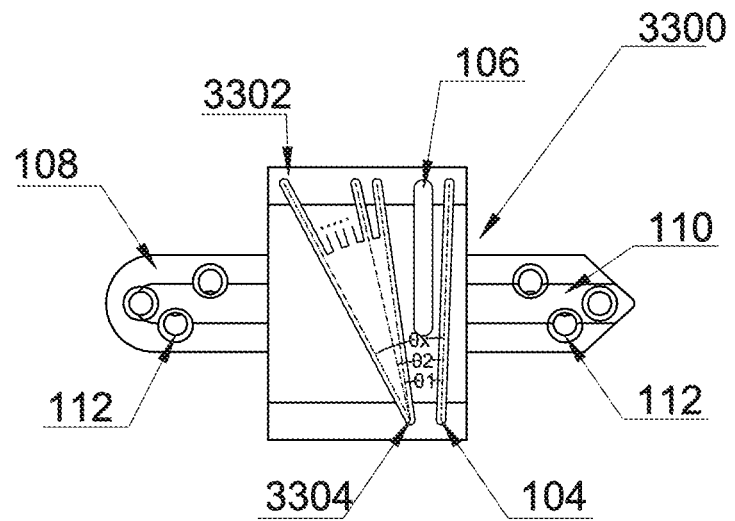
FIG. 33 is a diagram illustrating one embodiment of a surgical cutting block including a multi-cut guide and a single cut guide.

FIG. 33 is a diagram illustrating one embodiment of a surgical cutting block 3300 including a multi-cut guide 3304 and a single cut guide 104. In this embodiment, the multi-cut guide 3304 is located/positioned on the cutting platform 102 toward the cuneiform fixation platform 108 and the single cut guide 104 is located/positioned on a cutting platform 3202 toward the metatarsal fixation platform 110.

The multi-cut guide 3304 includes three or more paths that can include any suitable size and/or width capable of accepting a surgical cutting tool (e.g., a scalpel, surgical knife, etc.) and provide a respective path for the surgical cutting tool to follow while the surgical cutting tool is being used to produce an incision in a patient. The multi-cut guide 3304 includes an angle, which can be any suitable angle (e.g., an angle in the range of about one degree (1°) to about 90 degrees (90°)) with respect to any suitable reference point that can provide a predetermined and/or target path for the surgical cutting tool to follow while the surgical cutting tool is cutting a patient and/or performing a surgical procedure. Further, the angle between each respective pair of paths may be any suitable angle.

In some embodiments, the multi-cut guide 3304 and the single cut guide 104 are angled in the same direction (e.g., angled toward the left or toward the right with respect to the user (e.g., a medical professional)). In the illustrated embodiment, the multi-cut guide 3304 and the single cut guide 104 are angled in different directions.

In additional or alternative embodiments, the multi-cut guide 3304 and the single cut guide 104 are positioned on the cutting platform 1402 such that there is an angle ($\theta_1$), ($\theta_2$), and ($\theta_x$) created between the multi-cut guide 3304 and the single cut guide 104, which may be any suitable angle. In various embodiments, the respective angles ($\theta_1$), ($\theta_2$), and ($\theta_x$) may each be in the range of about 15° to about 75°.

Figure 34:
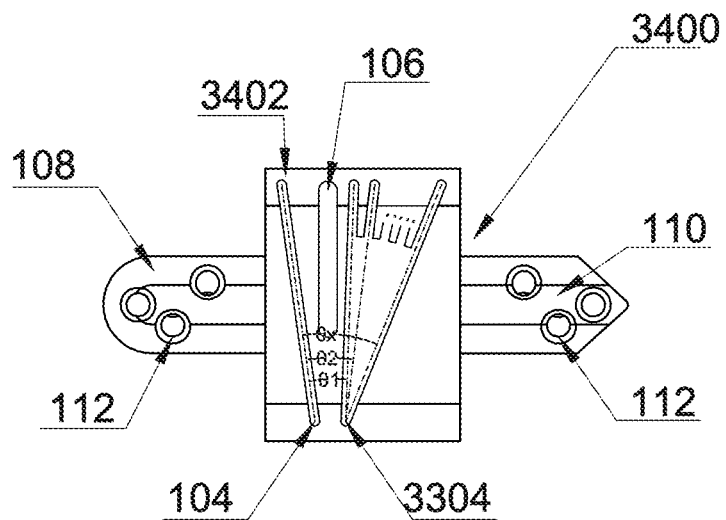
FIG. 34 is a diagram illustrating another embodiment of a surgical cutting block including a multi-cut guide and a single cut guide.

FIG. 34 is a diagram illustrating another embodiment of a surgical cutting block 3400 including a multi-cut guide 3304 and a single cut guide 104. In this embodiment, the multi-cut guide 3304 is located/positioned on a cutting platform 3402 toward the metatarsal fixation platform 110 and the single cut guide 104 is located/positioned on the cutting platform 3402 toward the cuneiform fixation platform 108.

In some embodiments, the multi-cut guide 3304 and the single cut guide 104 are angled in the same direction (e.g., angled toward the left or toward the right with respect to the user (e.g., a medical professional)). In the illustrated embodiment, the multi-cut guide 3304 and the single cut guide 104 are angled in different directions.

In additional or alternative embodiments, the multi-cut guide 3304 and the single cut guide 104 are positioned on the cutting platform 1402 such that there is an angle ($\theta_1$), ($\theta_2$), and ($\theta_x$) created between the multi-cut guide 3304 and the single cut guide 104, which may be any suitable angle. In various embodiments, the respective angles ($\theta_1$), ($\theta_2$), and ($\theta_x$) may each be in the range of about 15° to about 75°.

Figure 35:
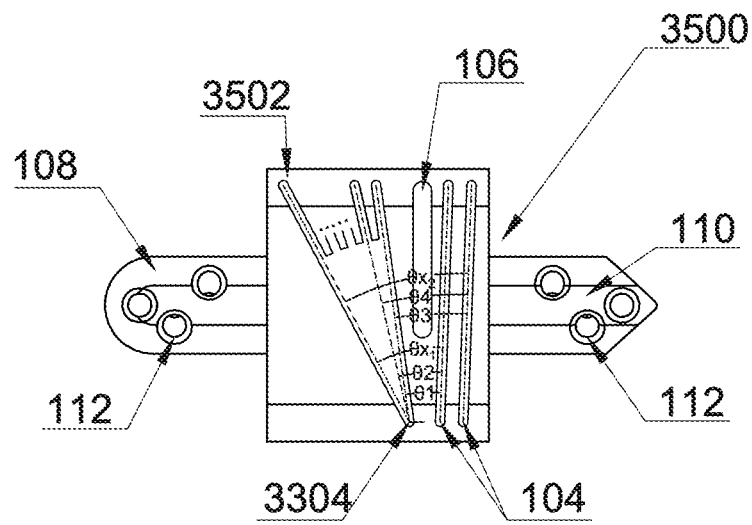
FIG. 35 is a diagram illustrating one embodiment of a surgical cutting block including a multi-cut guide and a plurality of single cut guides.

FIG. 35 is a diagram illustrating one embodiment of a surgical cutting block 3500 including a multi-cut guide 3304 and a plurality of single cut guides 104. In this embodiment, the multi-cut guide 3304 is located/positioned on a cutting platform 3502 toward the cuneiform fixation platform 108 and the plurality of single cut guides 104 are located/positioned on the cutting platform 3502 toward the metatarsal fixation platform 110.

In some embodiments, the multi-cut guide 3304 and the plurality of single cut guides 104 are angled in the same direction (e.g., angled toward the left or toward the right with respect to the user (e.g., a medical professional)). In the illustrated embodiment, the multi-cut guide 3304 and the plurality of single cut guides 104 are angled in different directions.

In additional or alternative embodiments, the multi-cut guide 3304 and the plurality of single cut guides 104 are positioned on the cutting platform 1402 such that there is an angle ($\theta_1$), ($\theta_2$), ($\theta_3$), ($\theta_4$), ($\theta_{x1}$), and ($\theta_{x2}$) created between the multi-cut guide 3304 and the plurality of single cut guides 104, which may be any suitable angle. In various embodiments, the respective angles ($\theta_1$), ($\theta_2$), ($\theta_3$), ($\theta_4$), ($\theta_{x1}$), and ($\theta_{x2}$) may each be in the range of about 15° to about 75°.

Figure 36:
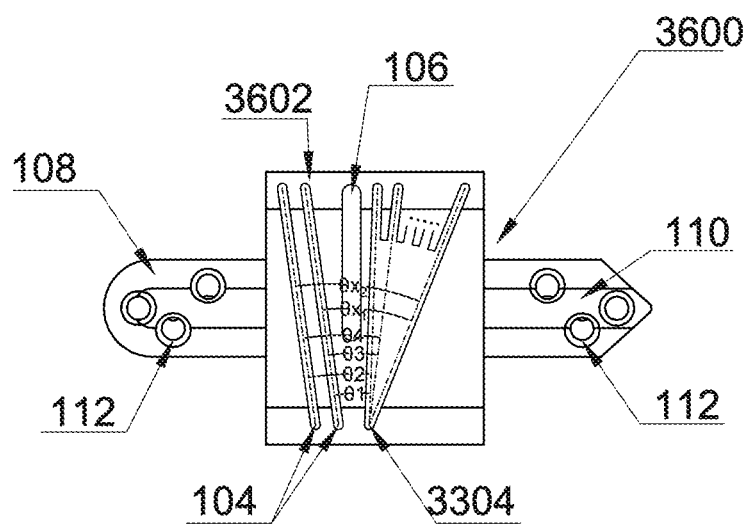
FIG. 36 is a diagram illustrating another embodiment of a surgical cutting block including a multi-cut guide and a plurality of single cut guides.

FIG. 36 is a diagram illustrating another embodiment of a surgical cutting block 3600 including a multi-cut guide 3304 and a plurality of single cut guides 104. In this embodiment, the multi-cut guide 3304 is located/positioned on a cutting platform 3602 toward the metatarsal fixation platform 110 and the plurality of single cut guides 104 are located/positioned on the cutting platform 3602 toward the cuneiform fixation platform 108.

In some embodiments, the multi-cut guide 3304 and the plurality of single cut guides 104 are angled in the same direction (e.g., angled toward the left or toward the right with respect to the user (e.g., a medical professional)). In the illustrated embodiment, the multi-cut guide 3304 and the plurality of single cut guides 104 are angled in different directions.

In additional or alternative embodiments, the multi-cut guide 3304 and the plurality of single cut guides 104 are positioned on the cutting platform 1402 such that there is an angle ($\theta_1$), ($\theta_2$), ($\theta_3$), ($\theta_4$), ($\theta_{x1}$), and ($\theta_{x2}$) created between the multi-cut guide 3304 and the plurality of single cut guides 104, which may be any suitable angle. In various embodiments, the respective angles ($\theta_1$), ($\theta_2$), ($\theta_3$), ($\theta_4$), ($\theta_{x1}$), and ($\theta_{x2}$) may each be in the range of about 15° to about 75°.

Figure 37:
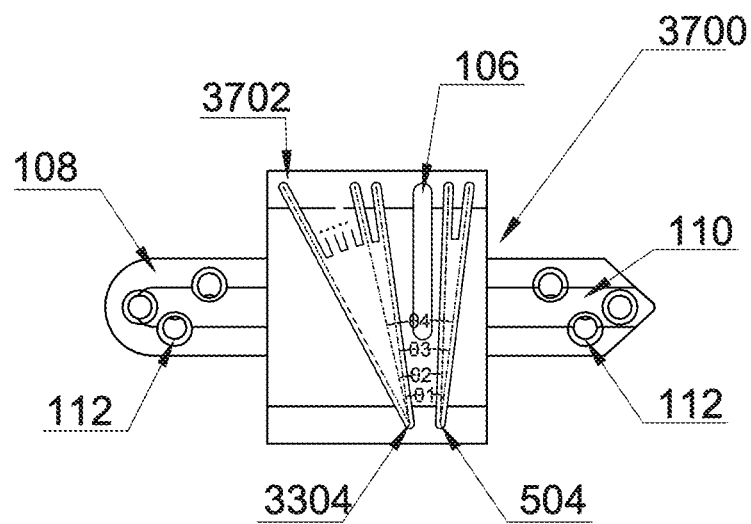
FIG. 37 is a diagram illustrating one embodiment of a surgical cutting block including a multi-cut guide and a double cut guide.

FIG. 37 is a diagram illustrating one embodiment of a surgical cutting block 3700 including a multi-cut guide 3304 and a double cut guide 504. In this embodiment, the multi-cut guide 3304 is located/positioned on a cutting platform 3702 toward the cuneiform fixation platform 108 and the double cut guide 504 is located/positioned on the cutting platform 3702 toward the metatarsal fixation platform 110.

In some embodiments, the multi-cut guide 3304 and the double cut guide 504 are angled in the same direction (e.g., angled toward the left or toward the right with respect to the user (e.g., a medical professional)). In the illustrated embodiment, the multi-cut guide 3304 and the double cut guide 504 are angled in different directions.

In additional or alternative embodiments, the multi-cut guide 3304 and the double cut guide 504 are positioned on the cutting platform 1402 such that there is an angle ($\theta_1$), ($\theta_2$), ($\theta_3$), ($\theta_4$), ($\theta_{x1}$), and ($\theta_{x2}$) created between the multi-cut guide 3304 and the double cut guide 504, which may be any suitable angle. In various embodiments, the respective angles ($\theta_1$), ($\theta_2$), ($\theta_3$), ($\theta_4$), ($\theta_{x1}$), and ($\theta_{x2}$) may each be in the range of about 15° to about 75°.

Figure 38:
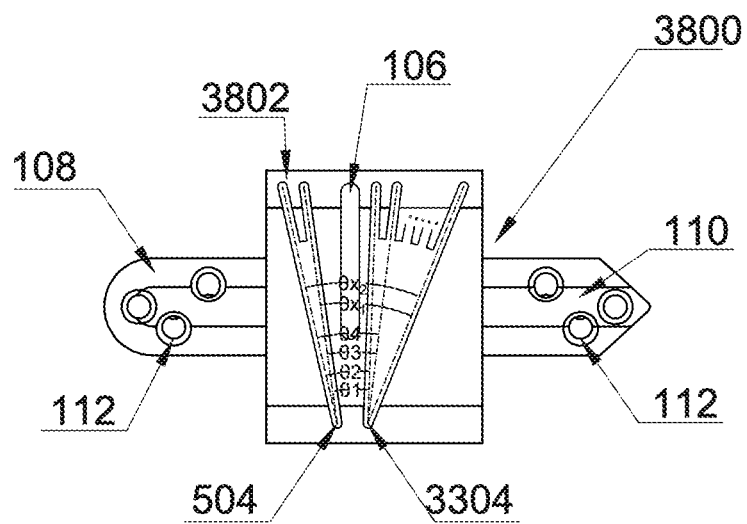
FIG. 38 is a diagram illustrating another embodiment of a surgical cutting block including a multi-cut guide and a double cut guide.

FIG. 38 is a diagram illustrating another embodiment of a surgical cutting block 3800 including a multi-cut guide 3304 and a double cut guide 504. In this embodiment, the multi-cut guide 3304 is located/positioned on a cutting platform 3802 toward the metatarsal fixation platform 110 and the double cut guide 504 is located/positioned on the cutting platform 3802 toward the cuneiform fixation platform 108.

In some embodiments, the multi-cut guide 3304 and the double cut guide 504 are angled in the same direction (e.g., angled toward the left or toward the right with respect to the user (e.g., a medical professional)). In the illustrated embodiment, the multi-cut guide 3304 and the double cut guide 504 are angled in different directions.

In additional or alternative embodiments, the multi-cut guide 3304 and the double cut guide 504 are positioned on the cutting platform 1402 such that there is an angle ($\theta_1$), ($\theta_2$), ($\theta_3$), ($\theta_4$), ($\theta_{x1}$), and ($\theta_{x2}$) created between the multi-cut guide 3304 and the double cut guide 504, which may be any suitable angle. In various embodiments, the respective angles ($\theta_1$), ($\theta_2$), ($\theta_3$), ($\theta_4$), ($\theta_{x1}$), and ($\theta_{x2}$) may each be in the range of about 15° to about 75°.

Figure 39:
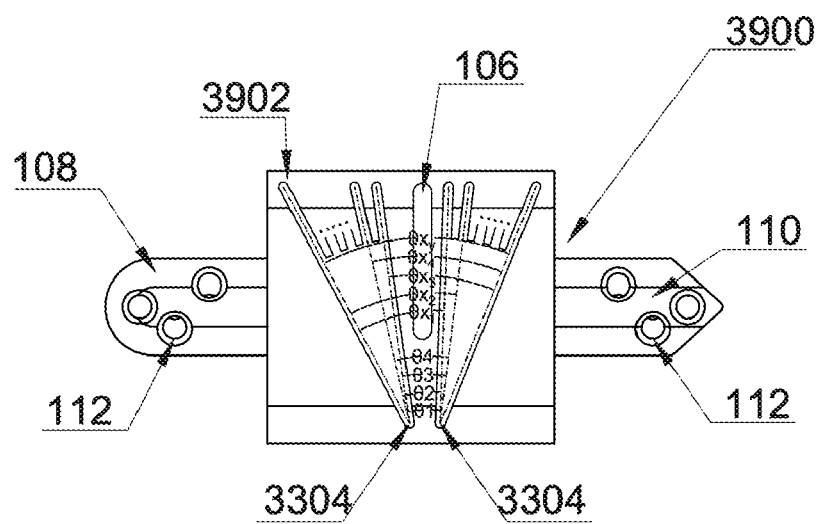
FIG. 39 is a diagram illustrating one embodiment of a surgical cutting block including a plurality of multi-cut guides.

FIG. 39 is a diagram illustrating one embodiment of a surgical cutting block 3900 including a plurality of multi-cut guides 3304. In this embodiment, a multi-cut guide 3304 is located/positioned on a cutting platform 3902 on both sides of the positioning slot 106.

In some embodiments, the multi-cut guides 3304 are angled in the same direction (e.g., angled toward the left or toward the right with respect to the user (e.g., a medical professional)). In the illustrated embodiment, the multi-cut guides 3304 are angled in different directions.

In additional or alternative embodiments, the multi-cut guides 3304 are positioned on the cutting platform 1402 such that there is an angle ($\theta_1$), ($\theta_2$), ($\theta_3$), ($\theta_4$), ($\theta_{x1}$), ($\theta_{x2}$), ($\theta_{x3}$), ($\theta_{x4}$), and ($\theta_{x5}$) created between the multi-cut guides 3304, which may be any suitable angle. In various embodiments, the respective angles ($\theta_1$), ($\theta_2$), ($\theta_3$), ($\theta_4$), ($\theta_{x1}$), ($\theta_{x2}$), ($\theta_{x3}$), ($\theta_{x4}$), and ($\theta_{x5}$) may each be in the range of about 15° to about 75°.

Figure 40A:
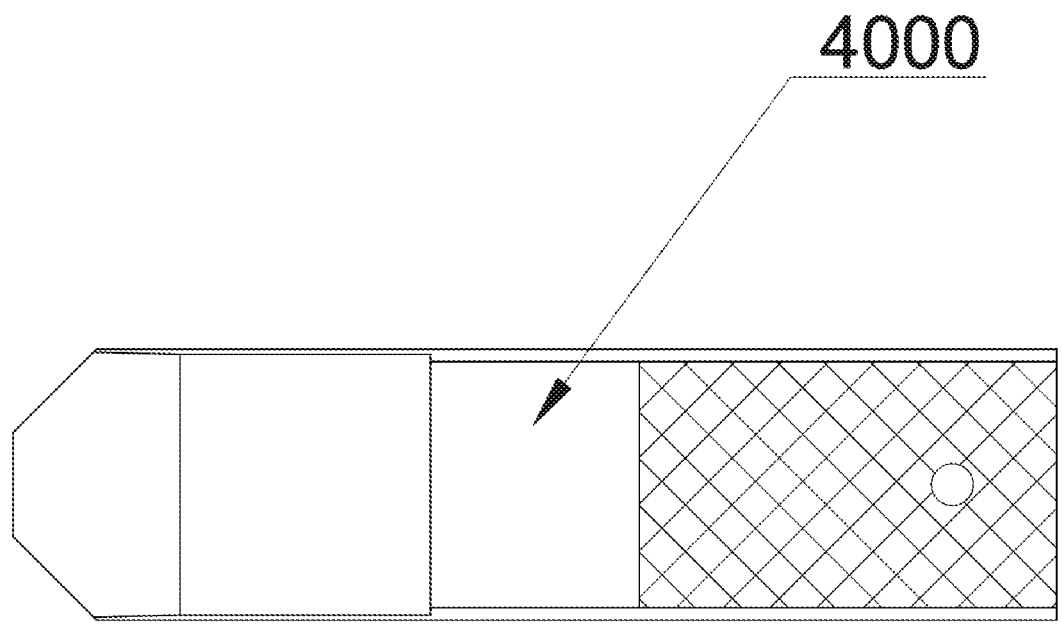
FIG. 40A is a diagram illustrating one embodiment of a positioning fin.

FIG. 40A is a diagram illustrating one embodiment of a positioning fin 4000. The positioning guide 4000 may include any shape and/or size that can be accommodated by a positioning slot 106.

Further, the positioning guide 4000 may include and/or be formed of any suitable material. In some embodiments, the positioning guide 4000 includes a sterilizable material.

Figure 40B:
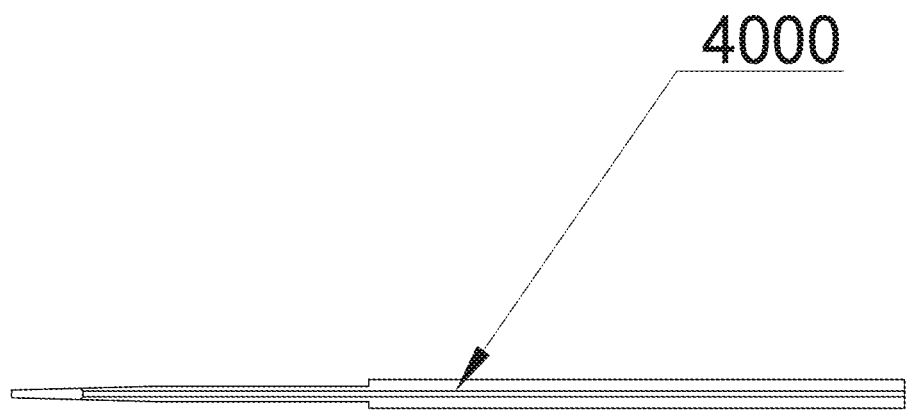
FIG. 40B is a diagram illustrating a profile view of the positioning fin illustrated in FIG. 40A.
Figure 41:
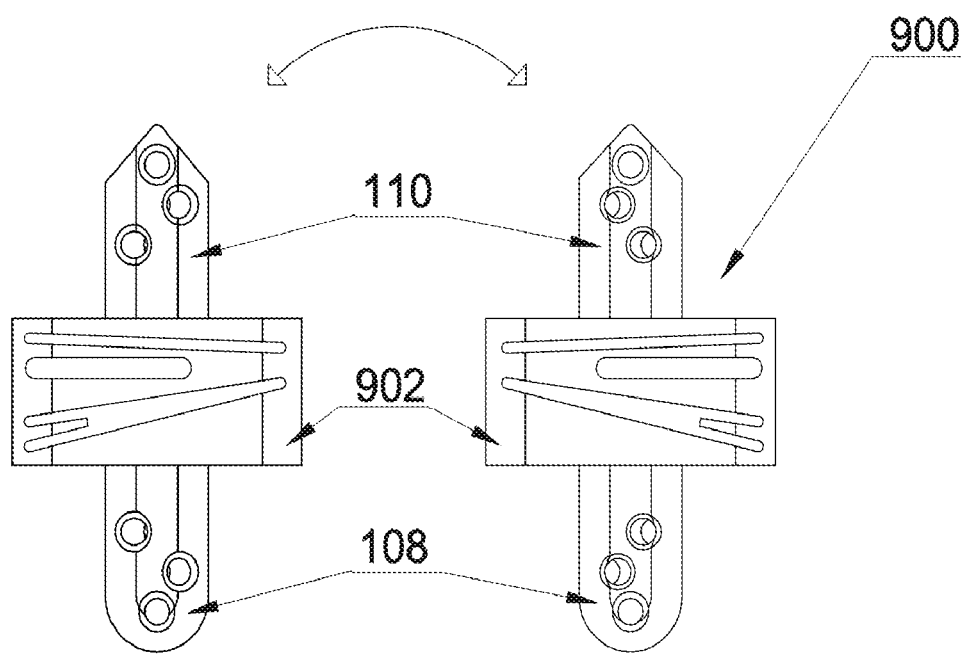
FIG. 41 is a diagram illustrating that opposite sides of a surgical cutting block can be used on the left foot and the right foot of a patient.

FIG. 40B is a diagram illustrating a profile view of the positioning fin illustrated in FIG. 40A. FIG. 41 is a diagram illustrating that opposite sides of surgical cutting blocks 100 through 3900 can be used on the left foot and/or the right foot of a patient.

The positioning guide 4000 and the positioning slot 106 are configured to cooperatively prepare a cuneiform-metatarsal joint for a surgical procedure. In some embodiments, the positioning guide 4000 and the positioning slot 106 are configured to cooperatively guide the positioning of a surgical cutting block (e.g., surgical cutting blocks 100 through 3900) at a cuneiform-metatarsal joint in preparation for a surgical procedure (e.g., a surgery to correct a bunion).

Figure 42A:
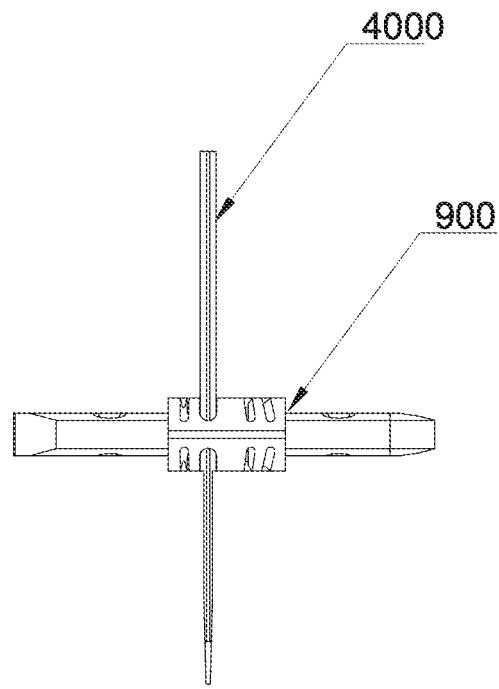
FIG. 42A is a diagram illustrating a profile view of one embodiment of a positioning fin and a surgical cutting board engaged with one another.
Figure 42B:
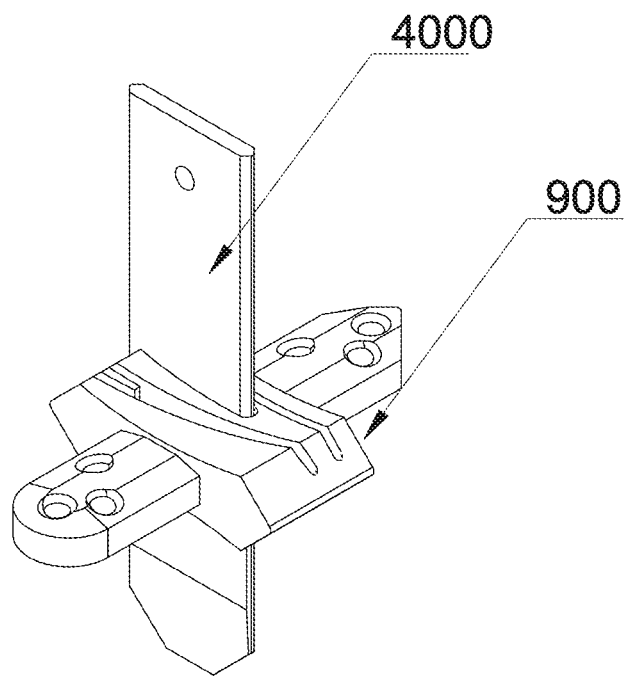
FIG. 42B is a diagram illustrating a closer view of the positioning fin and surgical cutting board illustrated in FIG. 42A.

A cutting platform (e.g., cutting platforms 102 through 3902) allows a cut guide (e.g., single cut guide(s) 104, double cut guide(s) 504, and/or multi-cut guide(s) 3304) to sit close to a bone surface. Surgical cutting blocks 100 through 3900 may be placed in the correct position by placing the positioning fin 4000 through the positioning slot 106 in the cutting portion (see, e.g., FIGS. 42A & 42B). The positioning fin 4000 is placed through the positioning slot 106 to allow the cut guide to placed centrally on a joint.

The cut guides are held in place using pins driven through the wire holes 112 into the cuneiform and metatarsal. Some wire holes 112 may include an angle while others are perpendicular to the surface of a cut guide.

The embodiments may be practiced in other specific forms. The described embodiments are to be considered in all respects only as illustrative and not restrictive. The scope of the technology is, therefore, indicated by the appended claims rather than by the foregoing description. All changes which come within the meaning and range of equivalency of the claims are to be embraced within their scope.

The invention claimed is:

1. A surgical cutting block, comprising:
   a quadrilateral shaped cutting platform including:
      a bottom surface, wherein at least a portion of the bottom surface includes a concave sloped portion;
      a top surface opposite the bottom surface, wherein at least a portion of the top surface includes a concave sloped portion;
         wherein the surgical cutting block is configured to be reversible and able to be used on a left foot of a patient and a right foot of a patient;
      a positioning slot formed on the cutting platform, the positioning slot dividing the cutting platform into a first side and a second side; and
      a double cut guide formed on the first side, wherein the double cut guide comprises a Y-shaped double cut guide.

2. The surgical cutting block of claim 1, further comprising a single cut guide formed on the second side.

3. The surgical cutting block of claim 2, wherein the single cut guide and the double cut guide are angled in different directions.

4. The surgical cutting block of claim 2, further comprising an angle between the single cut guide and the double cut guide.

5. The surgical cutting block of claim 4, wherein the angle between the single cut guide and the double cut guide is in the range of 15 degrees and 75 degrees.

6. The surgical cutting block of claim 2, further comprising:
   a first angle between the single cut guide and a first guide of the double cut guide; and
   a second angle between the single cut guide and a second guide of the double cut guide.

7. The surgical cutting block of claim 6, wherein:
   the first angle between the single cut guide and the double cut guide is in the range of 15 degrees and 75 degrees;
   the second angle between the single cut guide and the double cut guide is in the range of 15 degrees and 75 degrees; and
   the first angle and the second angle are different angles.

8. The surgical cutting block of claim 1, wherein the cutting platform further comprises a third sloped portion and a fourth sloped portion, wherein the third sloped portion and the fourth sloped portion can have one of the same and different slopes.

9. The surgical cutting block of claim 1, wherein the cutting platform comprises a third sloped portion.

10. A surgical cutting block, comprising:
    a quadrilateral shaped cutting platform including:
       a bottom surface, wherein at least a portion of the bottom surface includes a concave first sloped portion;
       a top surface opposite the bottom surface, wherein at least a portion of the top surface includes a concave second sloped portion;
       a positioning slot formed on the cutting platform; and
       a double cut guide formed on the cutting platform, wherein the double cut guide comprises a Y-shaped double cut guide.

11. The surgical cutting block of claim 10, wherein the cutting platform comprises a third sloped portion.

12. The surgical cutting block of claim 11, wherein the cutting platform further comprises a third sloped portion and a fourth sloped portion, wherein the third sloped portion and the fourth sloped can have one of the same and different slopes.

13. A surgical cutting device, comprising:
    attachment means; and
    a quadrilateral shaped cutting platform including:
       a bottom surface, wherein at least a portion of the bottom surface includes a concave sloped portion;
       a top surface opposite the bottom surface, wherein at least a portion of the top surface includes a concave sloped portion;
       a positioning slot formed on the cutting platform, the positioning slot dividing the cutting platform into a first side and a second side;
    wherein
       the first side comprises a first prong and a second prong, and
       the second side comprises a third prong.

14. The surgical cutting device of claim 13, wherein the attachment means comprises a set of apertures.

15. The surgical cutting device of claim 14, wherein each aperture is configured to receive a wire for attaching the surgical cutting device to a subject.

\* \* \* \* \*